(12) United States Patent
Anderson et al.

(10) Patent No.: US 6,753,420 B2
(45) Date of Patent: Jun. 22, 2004

(54) HIGH AFFINITY HUMANIZED ANTI-TAG-72 MONOCLONAL ANTIBODIES

(75) Inventors: W. H. Kerr Anderson, Midland, MI (US); Philip R. Tempest, West Wratting (GB); Frank J. Carr, Balmedie (GB); William J. Harris, Angus (GB); Kathryn Armour, West Wratting (GB)

(73) Assignee: The Dow Chemical Company, Midland, MI (US)

( * ) Notice: Subject to any disclaimer, the term of this patent is extended or adjusted under 35 U.S.C. 154(b) by 423 days.

(21) Appl. No.: 09/998,817

(22) Filed: Oct. 31, 2001

(65) Prior Publication Data

US 2003/0004318 A1 Jan. 2, 2003

Related U.S. Application Data

(60) Division of application No. 09/025,203, filed on Feb. 18, 1998, now Pat. No. 6,348,581, which is a continuation-in-part of application No. PCT/US97/19641, filed on Oct. 30, 1997, now abandoned.
(60) Provisional application No. 60/030,173, filed on Oct. 31, 1996, now abandoned.

(51) Int. Cl.$^7$ .............................................. C07H 21/04

(52) U.S. Cl. ............................ 536/23.53; 530/388.85; 530/387.3; 435/320.1

(58) Field of Search ........................... 536/23.53, 24.1; 435/325, 320.1; 530/387.1, 387.3, 388.85

(56) References Cited

U.S. PATENT DOCUMENTS

| 4,816,397 A | 3/1989 | Boss et al. |
|---|---|---|
| 4,816,567 A | 3/1989 | Cabilly et al. |
| 4,975,369 A | 12/1990 | Beavers et al. |
| 4,978,745 A | 12/1990 | Schoemaker et al. |
| 5,225,539 A | 7/1993 | Winter et al. |
| 5,435,990 A | 7/1995 | Cheng et al. |
| 5,472,693 A | 12/1995 | Gourlie et al. |
| 5,512,443 A | 4/1996 | Schlom et al. |
| 5,976,531 A | * 11/1999 | Mezes et al. |

FOREIGN PATENT DOCUMENTS

| EP | 0 365 997 B1 | 9/1994 |
|---|---|---|
| EP | 0 394 277 B1 | 1/1998 |

OTHER PUBLICATIONS

Amit, et al., "Three Dimensional Structure of an Antigen–Antibody Complex at 2.8 ÅResolution", Science, vol. 233, pp. 747–753 (1986).
Bebbington, et al., "High–Level Expression of a Recombinant Antibody From Myeloma Cells Using a Glutamine Synthetase Gene as an Amplifiable Selectable Marker", Bio/Technology, vol. 10, pp. 169–174 (1992).

Benhar, et al., "Rapid humanization of the Fv of monoclonal antibody B3 by using framework exchange of the recombinant immunotoxin B3(Fv)–PE38", Proc. Natl. Acad. Sci. USA, vol. 91, pp. 12051–12055 (1994).
Bulens, et al., "Construction and Characterization of a functional chimeric murine—human antibody directed against human fibrin fragment–D dimer", Eur. Journal Biochem, vol. 195, pp. 235–242 (1991).
Caron, et al., "Biological and Immunological Featues of Humanized M195 (Anti–CD33) Monoclonal Antibodies", Cancer Research, vol. 52, pp. 6761–6767 (1992).
Chaudhary, et al., "A recombinant immunotoxin consisting of two antibody variable domains fused to Pseudomonas exotoxin", Nature, vol. 339, pp. 394–397 (1989).
Chothia, et al., "Canonical Structures for the Hypervariable Regions of Immunoglobulins", Journal Molec. Biol., vol. 196, pp. 901–917 (1987).
Chothia, et al., "Conformations of immunoglobulin hypervariable regions", Nature, Vol 342, pp. 877–883 (1989).
Co, et al., "Humanized antibodies for therapy", Nature, vol. 351, pp. 501–502 (1991).
Colcher, et al., "A spectrum of monoclonal antibodies reactive with human mammary tumor cells", Proc. Natl. Acad. Sci. USA, vol. 78, No. 5, pp. 3199–3203 (1981).
Colcher, et al., "In Vivo Tumor Targeting of a Recombinant Single–Chain Antigen–Binding Protein", J. Natl. Cancer Inst., vol. vol. 82, No. 4, pp. 1191–1197 (1990).
Colcher, et al., "Characterization and Biodribution of Recombinant and Recombinant/Chimeric Constructs of Monoclonal Antibody B72.3", Cancer Research, vol. 49, pp. 1738–1745 (1989).
Colman, et al., "Three–dimensional structure of a complex of antibody with influenza virus neuraminidase", Nature, vol. 326, pp. 358–363 (1987).
Coloma, et al., "Novel vectors for the expression of antibody molecules using variable regions generated by polymerase chain reaction", Journal of Immunological Methods, vol. 152, pp. 89–104 (1992).
Couto, et al., "Humanization of KC4G3, an Anti–Human Carcinoma Antibody", Hybridoma, vol. 13, No. 3, pp. 215–219 (1994).
DeWaele, et al., "Expression in non–lymphoid cells of mouse recombinant immunoglobulin directed against the tumour marker human placental alkaline phosphatase", Eur. J. Biochem., vol. 176, pp. 287–295 (1988).
Dorai, et al., "Effect of Dihydrofolate Reductase–Mediated Gene Amplifiction on the Expression of Transfected Immunoglobulin Genes", The Journal of Immunology, vol. 139, No. 12, pp. 42321–4241 (1987).

(List continued on next page.)

Primary Examiner—Larry R. Helms

(57) ABSTRACT

Novel humanized monoclonal antibodies, humanized antibody fragments, and derivatives thereof which specifically bind TAG-72 are provided as well as methods for their manufacture. These humanized antibodies are useful in the treatment of cancers which express TAG-72 as well as for diagnostic purposes, e.g., for in vivo imaging of tumors or cancer cells which express TAG-72.

4 Claims, 14 Drawing Sheets

OTHER PUBLICATIONS

Fischmann et al., "Crystallographic Refinement fo the Three–dimensional Structure of the FabD1.3–Lysozyme Complex at 2.5A Resolution", The Journal of Biological Chemistry, vol. 266, No. 20, pp. 12915–12920 (1991).

Hinek, et al., "The Elastin Receptor: A Galactoside–Binding Protein", Science, vol. 239, pp. 1539–1541 (1988).

Hinkle, et al., "The Evolution of the Radioimmunoguided Surgery©System: An Innovative Technique for the Intraoperative Detection of Tumor", Antibody, Immunoconjugates, and Radiopharmaceuticals, vol. 4, No. 3, pp. 339–357 (1991).

Johnson, et al., "Analysis of a Human–Tumor–assocatiated Glycoprotein (TAG–72) Identified by Monoclonal Antibody B72.3", Cancer Research, vol. . 46, pp. 850–857 (1986).

Jones, et al., "Replacing the complementarity–determining regions in a human antibody with those from a mouse", Nature, vol. 321, pp. 522–525 (1986).

Kashmiri, et al., "Single–gene–encoded novel single–chain antibodies with anti–tumor cytolytic activity", XVI International Cancer Congress, vol. 1, pp. 183–187 (1994).

King, et al., "Expression, purification, and characterization of B72.3 Fv fragments", Biochem J., vol. 290, pp. 723–729 (1993).

LoBuglio, et al., "Mouse/human chimeric monoclonal antibody in man: Kinetics and immune response", Proc. Natl. Acad. Sci. USA, vol. 86, pp. 4420–4224 (1989).

Meredith, et al., "Pharnacokinetics, Immune Response, and Biodistribution of Iodine–131–Labeled Chimeric Mouse/Human lgG1,k 17–1A Monoclonal Antibody", The Journal of Nuclear Medicine, vol. 32, No. 6, pp. 1162–1168 (1991).

Milenic, et al., "construction, Binding Properties, Metabolism, and Tumor Targeting of a Single–Chain Fv Derived from the Pancarcinoma Monoclonal Antibody CC49", Cancer Research, vol. 51, pp. 6363–6371 (1991).

Molinolo, et al., "Enhanced Tumor Binding Using Immunohistochemical Analyses by Second Generation Anti–Tumor–associated Glycoprotein 72 Monoclonal Antibodies versus Monoclonal Antibody B72.3 in Human Tissue", Cancer Research, vol. 50, pp. 1291–1298 (1990).

Morrison, et al., "Chimeric human antibody molecules: Mouse antigen–binding domains with human constant region domains", Proc. Natl. Acad. Sci. USA, vol. 81, pp. 6851–6855 (1984).

Morrison, et al., "Gentically engineered Antibody Molecules", Advances in Immunology, vol. 44, pp. 65–91 (1989).

Muraro, et al., "Generation and Characterization of B72.3 Second Generation Monoclongal Antibodies Reactive with the Tumor–associated Glycoprotein 72 Antigen", Cancer Research , vol. 46, pp. 850–857 (1986).

Nishimura, et al., "Recombinant Human–Mouse Chimeric Monoclonal Antibody Specific for Common Acute Lymphocytic Leukemia Antigen", Cancer Research, vol. 47, pp. 999–1005 (1987).

O'Dwyer, et al., "Intraoperative Probe–Directed Immunodetection Using a Monoclonal Antibody", Arch Surg., vol. 121, pp. 1391–1394 (1986).

Page, et al., "High Level Expression of the Humanized Monoclonal Antibody Campath–1H in Chinese Hamster Ovary Cells", Bio/Technology, vol. 9, pp. 64–68 (1991).

Padlan, et al., "Structure of an antibody–antigen complex:Crystal structure of the HyHEL–10 Fab–lysozyme complex", Proc. Natl. Acad. Sci. USA, vol. 86, pp. 5938–5942 (1989).

Padlan, "A Possible Procedure for Reducing the Immunogenicity of Antibody Variable Domains While Preserving Their Ligand–Binding Properties", Molecular Immunology, vol. 28, No. 4/5, pp. 489–498 (1991).

Padlan, "Anatomy of the Antibody Molecule", Molecular Immunology, vol. 31, No. 3, pp. 169–217 (1994).

Queen, et al., "A humanized antibody that binds to the interleukin 2 receptor", Proc. Natl. Acad. Sci. USA, vol. 86, pp. 10029–10033 (1989).

Riechmann, et al., "Reshaping human anitbodies for therapy", Nature, vol. 332, pp. 323–327 (1988).

Saleh, "A phase II trial of murine monoclonal antibody 17–1A and interferon–$\gamma$: clinical and immunological data", Cancer Immunology Immunotherapy, vol. 32, pp. 185–190 (1990).

Sawyer, et al., "Theeffects of induction conditions on production of a soluble anti–tumor sFv in *Escherichia coli*", Protein Eng., vol. 7, No. 11, pp. 1401–1406 (1994).

Scatchard, "The Attractions of Proteins for Small Molecules and Ions", Annals of the New York Academy of Science, vol. 51, No. 4, pp. 660–672 (1949).

Sheriff, et al., "Three–dimensional structure of an antibody–antigen complex", Proc. NAtl. Acad. Sci. USA, vol. 84, pp. 8075–8079 (1987).

Shu, et al, "Secretion of a single–gene–encoded immunoglobulin from myeloma cells", Proc. Natil. Acad. Sci. USA, vol. 90, pp. 7995–7999 (1993).

Singer, "Optimal Humnaization of 1B4, an Anti–CD18 Murine Monoclonal antibody, is Achieved by Correct Choice of Human V–Region Framework Sequence", The Journal of Immunology, vol. 150, No. 7, pp. 2844–2857 (1993).

Slavin–Chiorini, et al., "Biologic Progerties of a $C_h2$ Domain–Deleted Recombinant Immunoglobulin", Int. Journal of Cancer, vol. 53, pp. 97–103 (1993).

Tempest, et al., "Reshaping a Human Monoclonal Antibody to Inhibit Human Respiratory Syncytial Virus Infection *In Vivo*", Bio/Technology, vol. 9, pp. 266–271 (1991).

Thor, et al., "Distribution of Oncofetal Antigen Tumor–associated Glycoprotein–72 Defined by Monocvlonal Antibody B72.3", Cancer Research, vol. 46, pp. 3118–3124 (1986).

Tulip, et al., "Refined Crystal Structure of the Influenza Virus N9 Neuramindase–NC41 Fab Complex", Journal Molec. Biol., vol. 227, pp. 122–148 (1992).

Tramontano, et al., "Framework Residue 71 is a Major Determinant of the Position and Conformation of the Second Hypervariable Region in the $V_H$ Domains of Immunoglobulins", Journal Molec. Biol., vol. 215, pp. 175–182 (1990).

Verhoeyen, et al., "Reshaping Human Antibodies: Grafting an Antilysozyme Activity", Science, vol. 239, pp. 1534–1536 (1988).

Weidle, et al., "Reconstitution of functionally aactive antibody directed against creatine kinase from separately expressed heavy and light chains in non–lymphoid cells", Gene, vol. 51, pp. 21–29 (1987).

Wood, et al., "High Level Synthesis of Immunologlubulins in Chinese Hamster Ovary Cells", The Journal of Immunology, vol. 145, pp. 3011–3016 (1990).

\* cited by examiner

FIG. 1

```
              10         20        A 30          40         50
              v          v          v            v          v
CC49MuVH   QVQLQQSDAELVKPGASVKISCKASGYTFTDHAIHWVKQNPEQGLEWIGYF
NEWMVH     QVQLQESGPGLVRPSQTLSLTCTVSG       WVRQPPGRGLEWIG
CC49NMVH   QVQLQESGPGLVRPSQTLSLTCTVSGYTFTDHAIHWVRQPPGRGLEWIGYF
              ^          ^       ↑ ↑          ^          ^
              10         20        30           40         50

60         70  K S  80           90         100
              v          v    v                v          v
CC49MuVH   SPGNDDFKYNERFKGKATLTADKSSSTAYVQLNSLTSEDSAVYFCTRSLNM
NEWMVH                     DTSKNQFSLRLSSVTAADTAVY
CC49NMVH   SPGNDDFKYNERFKGRVTMLADTSKNQFSLRLSSVTAADTAVYFCTRSLNM
              ^          ^↑         ^          ^       ↑↑  ^
              60         70         80         90         100

110
              v
CC49MuVH   AYWGQGTSVTVSS
NEWMVH       WGQGSLVTVSS
CC49NMVH   AYWGQGSLVTVSS
              ^
              110
```

FIG. 2

```
                     10          20          30          40          50
                      v           v           v           v           v
CC49MuVK    DIVMSQSPSSLPVSVGEKVTLSC|KSSQSLLYSGNQKNYLA|WYQQKPGQSPK
REIVK       DIQLTQSPSSLSASVGDRVTITC|KSS         KNYLA|WYQQTPGKAPK
CC49REVK    DIQMTQSPSSLSASVGDRVTITC|KSSQSLLYSGNQKNYLA|WYQQTPGKAPK
                      ^           ^           ^           ^           ^
                     10          20          30          40          50

60          70          80          90         100
                      v           v           v           v           v
CC49MuVK    LLIY|WASARES|GVPDRFTGSGSGTDFTLSISSVKTEDLAVYYC|QQYYSYPLT|
REIVK       LLIY|WA  ES|GVPSRFSGSGSGTDYTFTISSLQPEDIATYYC
CC49REVK    LLIY|WASARES|GVPSRFSGSGSGTDYTFTISSLQPEDIATYYC|QQYYSYPLT|
                ^           ^           ^           ^           ^
                     60          70          80          90         100

110
                     v
CC49MuVK    FGAGTKLVLK
REIVK       FGQGTKLQIT
CC49REVK    FGQGTKLQIT
                    ^
                    110
```

FIG. 3

Scotgen Heavy Chain Variable Region Comparison

```
CC49     Gln Val Gln Leu Gln Gln Ser Asp Ala Glu Leu Val Lys Pro
HuCC49   Gln Val Gln Leu Gln Glu Ser Gly Pro Gly Leu Val Arg Pro
NEWM     Gln Val Gln Leu Glu Gln Ser Gly Pro Gly Leu Val Arg Pro

CC49     Gly Ala Ser Val Lys Ile Ser Cys Lys Ala Ser Gly Tyr Thr
HuCC49   Ser Gln Thr Leu Ser Leu Thr Cys Thr Val Ser Gly Tyr Thr
NEWM     Ser Gln Thr Leu Ser Leu Thr Cys Thr Val Ser Gly Ser Thr
                                CDR1
CC49     Phe Thr |Asp His Ala Ile His| Trp Val Lys Gln Asn Pro Glu
HuCC49   Phe Thr |Asp His Ala Ile His| Trp Val Arg Gln Pro Pro Gly
NEWM     Phe Ser |Asn Asp Tyr Tyr Thr| Trp Val Arg Gln Pro Pro Gly
                                                              CDR2
CC49     Gln Gly Leu Glu Trp Ile Gly |Tyr Phe Ser Pro Gly Asn Asp
HuCC49   Arg Gly Leu Glu Trp Ile Gly |Tyr Phe Ser Pro Gly Asn Asp
NEWM     Arg Gly Leu Glu Trp Ile Gly |Tyr Val Phe  -  Tyr His Gly

CC49     Asp Phe Lys Tyr Asn Glu Arg Phe Lys Gly| Lys Ala Thr Leu
HuCC49   Asp Phe Lys Tyr Asn Glu Arg Phe Lys Gly| Arg Val Thr Met
NEWM     Thr Ser Asp Asp Thr Thr Pro Leu Arg Ser| Arg Val Thr Met

CC49     Thr Ala Asp Lys Ser Ser Ser Thr Ala Tyr Val Gln Leu Asn
HuCC49   Leu Ala Asp Thr Ser Lys Asn Gln Phe Ser Leu Arg Leu Ser
NEWM     Leu Val Asp Thr Ser Lys Asn Gln Phe Ser Leu Arg Leu Ser

CC49     Ser Leu Thr Ser Glu Asp Ser Ala Val Tyr Phe Cys Thr Arg
HuCC49   Ser Val Thr Ala Ala Asp Thr Ala Val Tyr Phe Cys Thr Arg
NEWM     Ser Val Thr Ala Ala Asp Thr Ala Val Tyr Tyr Cys Ala Arg
                           CDR3
CC49     Ser Leu Asn Met Ala Tyr  -   -   -  | Trp Gly Gln Gly Thr
HuCC49   Ser Leu Asn Met Ala Tyr  -   -   -  | Trp Gly Gln Gly Ser
NEWM     Asn Leu Ile Ala Gly Cys Ile Asp Val | Trp Gly Gln Gly Ser

CC49     Ser Val Thr Val Ser Ser
HuCC49   Leu Val Thr Val Ser Ser
NEWM     Leu Val Thr Val Ser Ser
```

FIG. 4

Scotgen Light Chain Variable Region Comparison

```
CC49     Asp Ile Val Met Ser Gln Ser Pro Ser Ser Leu Pro Val Ser
HuCC49   Asp Ile Gln Met Thr Gln Ser Pro Ser Ser Leu Ser Ala Ser
REI      Asp Ile Gln Met Thr Gln Ser Pro Ser Ser Leu Ser Ala Ser

CC49     Val Gly Glu Lys Val Thr Leu Ser Cys|Lys Ser Ser Gln Ser
HuCC49   Val Gly Asp Arg Val Thr Ile Thr Cys|Lys Ser Ser Gln Ser
REI      Val Gly Asp Arg Val Thr Ile Thr Cys|Gln Ala Ser Gln  -
                               CDR1
CC49     Leu Leu Tyr Ser Gly Asn Gln Lys Asn Tyr Leu Ala|Trp Tyr
HuCC49   Leu Leu Tyr Ser Gly Asn Gln Lys Asn Tyr Leu Ala|Trp Tyr
REI        -   -   -   -   -  Asp Ile Ile Lys Tyr Leu Asn|Trp Tyr

CC49     Gln Gln Lys Pro Gly Gln Ser Pro Lys Leu Leu Ile Tyr|Trp
HuCC49   Gln Gln Thr Pro Gly Lys Ala Pro Lys Leu Leu Ile Tyr|Trp
REI      Gln Gln Thr Pro Gly Lys Ala Pro Lys Leu Leu Ile Tyr|Glu
                  CDR2
CC49     Ala Ser Ala Arg Glu Ser|Gly Val Pro Asp Arg Phe Thr Gly
HuCC49   Ala Ser Ala Arg Glu Ser|Gly Val Pro Ser Arg Phe Ser Gly
REI      Ala Ser Asn Leu Gln Ala|Gly Val Pro Ser Arg Phe Ser Gly

CC49     Ser Gly Ser Gly Thr Asp Phe Thr Leu Ser Ile Ser Ser Val
HuCC49   Ser Gly Ser Gly Thr Asp Tyr Thr Phe Thr Ile Ser Ser Leu
REI      Ser Gly Ser Gly Thr Asp Tyr Thr Phe Thr Ile Ser Ser Leu

CC49     Lys Thr Glu Asp Leu Ala Val Tyr Tyr Cys|Gln Gln Tyr Tyr
HuCC49   Gln Pro Glu Asp Ile Ala Thr Tyr Tyr Cys|Gln Gln Tyr Tyr
REI      Gln Pro Glu Asp Ile Ala Thr Tyr Tyr Cys|Gln Gln Tyr Gln
              CDR3
CC49     Ser Tyr Pro Leu Thr|Phe Gly Ala Gly Thr Lys Leu Val Leu
HuCC49   Ser Tyr Pro Leu Thr|Phe Gly Gln Gly Thr Lys Leu Gln Ile
REI      Ser Leu Pro Tyr Thr|Phe Gly Gln Gly Thr Lys Leu Gln Ile

CC49     Lys
HuCC49   Thr
REI      Thr
```

Mammalian Cell Vectors for the Expression of Humanized V Regions

ELISA Showing Binding of CC49 Antibodies to TAG72

FIG. 13

```
        270             280             290                 300
         v               v               v                   v
CAG GTC CAA CTG CAG GAG AGC GGT CCA GGT CTT GTG AGA CCT AGC CAG 310             320             330                     370
   v               v               v                       v
ACC CTG AGC CTG ACC TGC ACC GTG TCT GGC...    ...TGG GTG AGA CAG 380             390             400                     480
   v               v               v                       v
CCA CCT GGA CGA GGT CTT GAG TGG ATT GGA...    ...GAC ACC AGC AAG 490             500             510             520     530
   v               v               v               v       v
AAC CAG TTC AGC CTG AGA CTC AGC AGC GTG ACA GCC GCC GAC ACC GCG 540                         580             590         600
   v                           v               v           v
GTC TAT...   ...TGG GGC CAA GGG TCC TTG GTC ACC GTC TCC TCA
```

FIG. 14

```
            270             280             290             300
             v               v               v               v
CAG GTC CAA CTG CAG GAG AGC GGT CCA GGT CTT GTG AGA CCT AGC CAG
GTC CAG GTT GAC GTC CTC TCG CCA GGT CCA GAA CAC TCT GGA TCG GTC 310             320             330             340             350
       v               v               v               v               v
ACC CTG AGC CTG ACC TGC ACC GTG TCT GGC TAC ACC TTC ACT GAC CAT
TGG GAC TCG GAC TGG ACG TGG CAC AGA CCG ATG TGG AAG TGA CTG GTA 360             370             380             390             400
       v               v               v               v               v
GCA ATT CAC TGG GTG AGA CAG CCA CCT GGA CGA GGT CTT GAG TGG ATT
CGT TAA GTG ACC CAC TCT GTC GGT GGA CCT GCT CCA GAA CTC ACC TAA 410             420             430             440             450
       v               v               v               v               v
GGA TAT TTT TCT CCC GGA AAT GAT GAT TTT AAA TAC AAT GAG AGG TTC
CCT ATA AAA AGA GGG CCT TTA CTA CTA AAA TTT ATG TTA CTC TCC AAG 460             470             480             490             500
             v               v               v               v               v
AAG GGG AGA GTG ACA ATG CTG GCA GAC ACC AGC AAG AAC CAG TTC AGC
TTC CCC TCT CAC TGT TAC GAC CGT CTG TGG TCG TTC TTG GTC AAG TCG 510             520             530             540
             v               v               v               v
CTG AGA CTC AGC AGC GTG ACA GCC GCC GAC ACC GCG GTC TAT TTC TGT
GAC TCT GAG TCG TCG CAC TGT CGG CGG CTG TGG CGC CAG ATA AAG ACA 550             560             570             580             590
 v               v               v               v               v
ACA AGA TCC CTG AAT ATG GCC TAC TGG GGC CAA GGG TCC TTG GTC ACC
TGT TCT AGG GAC TTA TAC CGG ATG ACC CCG GTT CCC AGG AAC CAG TGG 600
 v
GTC TCC TCA
CAG AGG AGT
```

HIGH AFFINITY HUMANIZED ANTI-TAG-72 MONOCLONAL ANTIBODIES

CROSS-REFERENCE TO RELATED APPLICATIONS

The present Application is a Division of U.S. patent Application Ser. No. 09/025,203, filed Feb. 18, 1998, now U.S. Pat. No. 6,348,581, which is a Continuation-in-Part of International Application Serial No. PCT/US97/19641, filed Oct. 30, 1997 designating the United States, now abandoned, which is a Continuation-in-Part of U.S. Provisional Patent Application Serial No. 60/030,173, filed Oct. 31, 1996, now abandoned.

FIELD OF THE INVENTION

The present invention relates to humanized monoclonal antibodies and fragments or derivatives thereof which specifically bind tumor-associated glycoprotein TAG-72, a human pancarcinoma antigen expressed by various human tumor cells. More specifically, the present invention relates to humanized monoclonal antibodies and fragments or derivatives thereof derived from murine monoclonal antibody CC49 or other murine antibodies which specifically bind TAG-72. The present invention further relates to methods for producing such humanized monoclonal antibodies specific to TAG-72, pharmaceutical and diagnostic compositions containing such humanized monoclonal antibodies, and methods of use thereof for the treatment or diagnosis of cancer.

BACKGROUND OF THE INVENTION

The identification of antigens expressed by tumor cells and the preparation of monoclonal antibodies which specifically bind such antigens is well known in the art. Anti-tumor monoclonal antibodies exhibit potential application as both therapeutic and diagnostic agents. Such monoclonal antibodies have potential application as diagnostic agents because they specifically bind tumor antigens and thereby can detect the presence of tumor cells or tumor antigen in an analyte. For example, use of monoclonal antibodies which bind tumor antigens for in vitro and in vivo imaging of tumor cells or tumors using a labeled form of such a monoclonal antibody is conventional in the art.

Moreover, monoclonal antibodies which bind tumor antigens have well known application as therapeutic agents. The usage of monoclonal antibodies themselves as therapeutic agents, or as conjugates wherein the monoclonal antibody is directly or indirectly attached to an effector moiety, e.g., a drug, cytokine, cytotoxin, etc., is well known.

Essentially, if the monoclonal antibody is attached to an effector moiety the monoclonal antibody functions as a targeting moiety, i.e. it directs the desired effector moiety (which typically possesses therapeutic activity) against a desired target, e.g., a tumor which expresses the antigen bound by the monoclonal antibody. In contrast, when the monoclonal antibody itself operates as a therapeutic agent, the antibody functions both as a targeting moiety—i.e., it will specifically bind a cell which expresses the antigen— and as an effector which mediates therapeutic activity, typically tumor cell lysis. Such effector functions— including, e.g., antibody-dependent cellular cytotoxicity (ADCC) and complement dependent cytotoxicity (CDC), among others—are effected by the portion of the antibody molecule generally referred to in the literature as the Fc portion. One specific tumor antigen against which various monoclonal antibodies have been developed is tumor-associated glycoprotein TAG-72. TAG-72 is expressed on the surface of various human tumor cells, such as the LS174T tumor cell line (American Type Tissue Collection (ATCC) No. CL188, a variant of cell line LS180 (ATCC No. CL187)), a colon adenocarcinoma line. Various research groups have reported the production of monoclonal antibodies to TAG-72. See, e.g., Muraro et al., *Cancer Res.*, 48:4588–4596 (1988); Johnson et al., *Cancer Res.*, 46:850–857 (1986); Molinolo et al., *Cancer Res.*, 50:1291–1298 (1990); Thor et al., *Cancer Res.*, 46:3118–3127 (1986); EP 394,277 to Schlom et al. (assigned to the National Cancer Institute); and U.S. Pat. No. 5,512,443 to Jeffrey Schlom et al. Specific antibodies to TAG-72 which are publicly available include CC49 (ATCC No. HB 9459), CC83 (ATCC No. HB 9453), CC46 (ATCC No. HB 9458), CC92 (ATCC No. HB 9454), CC30 (ATCC No. HB 9457), CC11 (ATCC No. 9455), and CC15 (ATCC No. HB 9460).

One example thereof, CC49, is a murine monoclonal antibody of the $IgG_1$ isotype. This monoclonal antibody is a second generation monoclonal antibody prepared by immunizing mice with TAG-72 purified using the first generation antibody B72.3. Colcher et al., *Proc. Natl. Acad. Sci. USA*, 78:3199–3203 (1981). CC49 specifically binds TAG-72, and has a higher antigen-binding affinity than B72.3. Muraro et al., *Cancer Res.*, 48:4588–4596 (1988). This monoclonal antibody has been reported to target human colon carcinoma xenografts efficiently, and to reduce the growth of such xenografts with good efficacy. Molinolo et al., *Cancer Res.*, 50:1291–1298 (1996); Colcher et al., *J. Natl. Cancer Inst.*, 82:1191–1197 (1990). Also, radiolabeled CC49 has been reported to exhibit excellent tumor localization in several ongoing clinical trials.

However, while murine antibodies have applicability as therapeutic agents in humans, they are disadvantageous in some respects. Specifically, murine antibodies, because of the fact that they are of foreign species origin, may be immunogenic in humans. This may result in a neutralizing antibody response (human anti-murine antibody (HAMA) response), which is particularly problematic if the antibodies are desired to be administered repeatedly, e.g., in treatment of a chronic or recurrent disease condition. Also, because they contain murine constant domains they may not exhibit human effector functions.

In an effort to eliminate or reduce such problems, chimeric antibodies have been disclosed. Chimeric antibodies contain portions of two different antibodies, typically of two different species. Generally, such antibodies contain human constant regions and variable regions of another species, typically murine variable regions. For example, some mouse/human chimeric antibodies have been reported which exhibit binding characteristics of the parental mouse antibody, and effector functions associated with the human constant region. See, e.g.: U.S. Pat. No. 4,816,567 to Cabilly et al.; U.S. Pat. No. 4,978,745 to Shoemaker et al.; U.S. Pat. No. 4,975,369 to Beavers et al.; and U.S. Pat. No. 4,816,397 to Boss et al. Generally, these chimeric antibodies are constructed by preparing a genomic gene library from DNA extracted from pre-existing murine hybridomas. Nishimura et al., *Cancer Res.*, 47:999 (1987). The library is then screened for variable region genes from both heavy and light chains exhibiting the correct antibody fragment rearrangement patterns. Alternatively, cDNA libraries are prepared from RNA extracted from the hybridomas and screened, or the variable regions are obtained by polymerase chain reaction. The cloned variable region genes are then ligated into an expression vector containing cloned cassettes of the appropriate heavy or light chain human constant region gene. The chimeric genes are then expressed in a cell line of choice, usually a murine myeloma line. Such chimeric antibodies have been used in human therapy.

Moreover, the production of chimeric mouse-human antibodies derived from CC49 and CC83, which specifically bind TAG-72, has been reported. In this regard, see e.g., EPO 0,365,997 to Mezes et al. (The Dow Chemical Company). One such chimeric CC49 antibody is that produced by the cell line deposited as ATTC No. HB 9884 (Budapest).

Also, Morrison et al. report the preparation of several antitumor chimeric monoclonal antibodies, in *Important Advances in Oncology, Recombinant Chimeric Monoclonal Antibodies*, pp. 3–18 (S. A. Rosenberg, ed., 1990) (J. B. Lippincott, Philadelphia, Pa.). Results of clinical trials with chimeric cMAb-17-1A in patients with metastatic colorectal carcinoma now show that this antibody has a 6-fold longer circulation time and significantly reduced immunogenicity as compared to the murine monoclonal antibody from which it was derived. LoBuglio et al., *Proc. Natl. Acad. Sci. USA*, 86:4220–4224 (1989); Meredith et al., *J. Nucl. Med.*, 32:1162–1168 (1991).

However, while such chimeric monoclonal antibodies typically exhibit lesser immunogenicity, they are still potentially immunogenic in humans because they contain murine variable sequences which may elicit antibody responses. Thus, there is the possibility that these chimeric antibodies may elicit an anti-idiotypic response if administered to patients. Saleh et al., *Cancer Immunol. Immunother.*, 32:185–190 (1990).

For example, when cB72.3(γ4) was administered to patients with colorectal carcinomas, 62% of such patients elicited a human antimurine antibody (HAMA) response, which included an anti-V-region response. This is disadvantageous because a HAMA response would make repeated antitumor antibody administration potentially ineffective because of an increased antibody clearance from the serum (Saleh et al., *Cancer Immunol. Immunother.*, 32:180–190 (1990)) and also because of potential allergic reactions (LoBuglio et al., *Hybridoma*, 5:5117–5123 (1986)).

A number of genetic variants of potential clinical utility have been developed from MAb CC49. These include cCC49, a $C_H2$ domain-deficient cCC49 (Slavin-Chiorini et al, *Int. J. Cancer*, 53:97–103 (1993)), and a single chain Fv (sFv) (Milenic et al., *Cancer Res.*, 51:6365–6371 (1991); Sawyer et al., *Protein Eng.*, 7:1401–1406 (1994)). These molecules may elicit relatively reduced HAMA responses in patients, since they have shown more rapid plasma and whole body clearance rates in mice and rhesus monkeys, as compared to intact IgG. Slavin-Chiorini et al. (1993) (id.); Milenic et al. (1991) (id.). Additionally, novel single-chain immunoglobulin (SC1 g) molecules derived from cCC49 have been reported and are encoded by single-gene constructs. One such molecule, $SCIg\Delta C_H1$ consists of CC49 sFv linked to the human γ1 Fc region (Shu et al., *Proc. Natl. Acad. Sci. USA*, 90:7995–7999 (1993)) while the other SCIg-IL-2 carries a human interleukin-2 (IL-2) molecule genetically attached to the carboxyl end of the Fc region of $SCIg\Delta C_H1$ (Kashmiri et al., *Proc. XVI Intl. Cancer Cong.*, 1:183–187 (1994)). Both SCIgs are comparable to cCC49 in antigen binding and antibody cellular cytolytic activity. The biological activity of the IL-2 is also retained in SCIg-IL-2.

In an effort to alleviate the immunogenicity concerns of chimeric and murine antibodies, the production of "humanized" antibodies is also known. Ideally, "humanization" results in an antibody that is non-immunogenic in humans, with substantially complete retention of the antigen-binding properties of the original molecule. In order to retain all the antigen-binding properties of the original antibody, the structure of its combining-site has to be faithfully reproduced in the "humanized" version. This can potentially be achieved by transplanting the combining site of the nonhuman antibody onto a human framework, either (a) by grafting only the nonhuman CDRs onto human framework and constant regions with or without retention of critical framework residues (Jones et al., *Nature*, 321:522 (1986); Verhoeyen et al., *Science*, 239:1539 (1988)); or (b) by transplanting the entire nonhuman variable domains (to preserve ligand-binding properties) but also "cloaking" them with a human-like surface through judicious replacement of exposed residues (to reduce antigenicity) (Padlan, *Molec. Immunol.*, 28:489 (1991)).

Essentially, humanization by CDR grafting involves transplanting only the CDRs onto human fragment and constant regions. Theoretically, this should substantially eliminate immunogenicity (except if allotypic or idiotypic differences exist). Jones et al., *Nature*, 321:522–525 (1986); Verhoeyen et al., *Science*, 239:1534–1536 (1988); Riechmann et al., *Nature*, 332:323–327 (1988). While such a technique is effective in some instances, CDR-grafting sometimes does not yield the desired result. Rather, it has been reported that some framework residues of the original antibody may also need to be preserved in order to preserve antigen binding activity. Riechmann et al., *Nature*, 332:323–327 (1988); Queen et al., *Proc. Natl. Acad. Sci. USA*, 86:10023–10029; Tempest et al., *Biol. Technology*, 9:266–271 (1991); Co et al., *Nature*, 351:501–502 (1991)).

As discussed, in order to preserve the antigen-binding properties of the original antibody, the structure of its combining site must be faithfully reproduced in the humanized molecule. X-ray crystallographic studies have shown that the antibody combining site is built primarily from CDR residues, although some neighboring framework residues have been found to be involved in antigen binding. Amit et al., *Science*, 233:747–753 986); Colman et al., *Nature*, 326:358–363 (1987); Sheriff et al., *Proc. Natl. Acad. Sci. USA*, 84:8075–8079 (1987); Padlan et al., *Proc. Natl. Acad Sci. USA*, 86:5938–5942 (1989); Fischmann et al., *J. Biol. Chem.*, 266:12915–12920 (1991); Tulip et al., *J. Molec. Biol.*, 227:122–148 (1992). It has also been found that the structures of the CDR loops are significantly influenced by surrounding framework structures. Chothia et al., *J. Molec. Biol.*, 196:901–917 (1987); Chothia et al., *Nature*, 342:877–883 (1989); Tramomonteno et al., *J. Molec. Biol*, 215:175–182 (1990).

Small but significant differences in the relative disposition of the variable light chain ($V_L$) and variable heavy ($V_H$) domains have been noted (Colman et al., *Nature*, 326:358–363 (1987)) and those differences are ostensibly due to variations in the residues involved in the interdomain contact (Padlan et al., *Molec. Immunol.*, 31:169–217 (1994)).

Furthermore, structural studies of the effect of the mutation of interior residues, in which changes in side chain volume are involved, have shown that the resulting local deformations are accommodated by shifts in side chain positions that are propagated to distant parts of the molecular interior. This suggests that during humanization the interior residues in the variable domains and in the interface between these domains, or at least the interior volumes, should also be maintained; a humanization protocol in which an interior residue is replaced by one of different physical properties (such as size, charge, or hydrophobicity, etc.), could result in a significant modification of the antigen combining site structure.

One method of identifying the framework residues which need to be preserved is by computer modeling. Alternatively, critical framework residues may potentially be identified by comparing known antibody combining site structures (Padlan, *Molec. Immun.*, 31(3):169–217 (1994)).

The residues which potentially affect antigen binding fall into several groups. The first group comprises residues that are contiguous with the combining site surface and which could therefore make direct contact with antigens. They include the amino-terminal residues and those adjacent to the CDRs. The second group includes residues that could alter the structure or relative alignment of the CDRs either by contacting the CDRs or the opposite chains. The third group comprises amino acids with buried side chains that could influence the structural integrity of the variable domains. The residues in these groups are usually found in the same positions (ibid.) according to the adopted numbering system. See Kabat et al., *Sequences of Proteins of Immunological Interest*, NIH Pub. No. 91–3242 (5th ed., 1991) (U.S. Dept. Health & Human Services, Bethesda, Md.) and Genbank.

However, while humanized antibodies are desirable because of their potential low immunogenicity in humans, their production is unpredictable. For example, sequence modification of antibodies may result in substantial or even total loss of antigen binding affinity, or loss of binding specificity. Alternatively, "humanized antibodies" may still exhibit immunogenicity in humans, irrespective of sequence modification.

Thus, there still exists a significant need in the art for novel humanized antibodies to desired antigens. More specifically, there exists a need in the art for humanized antibodies specific to TAG-72, because of their potential as immunotherapeutic and immunodiagnostic agents.

OBJECTS OF THE INVENTION

Toward this end, it is an object of the invention to provide humanized antibodies which are specific to human TAG-72.

More specifically, it is an object of the invention to provide humanized antibodies derived from murine antibodies to TAG-72, and in particular from CC49, a specific murine antibody which binds to TAG-72.

It is also an object of the invention to provide pharmaceutical compositions containing humanized antibodies which are specific to TAG-72. It is a more specific object of the invention to provide pharmaceutical compositions containing humanized antibodies derived from CC49, a murine antibody which specifically binds to TAG-72.

It is another specific object of the invention to provide methods of using humanized antibodies to TAG-72 for treatment of cancers which express TAG-72, in particular human colon cancer.

It is another object of the invention to provide immunodiagnostic compositions for detecting cancer cells which contain a humanized antibody which specifically binds TAG-72, and preferably is derived from CC49, which antibody is in labeled or unlabeled form. It is another object of the invention to provide a method of immunodiagnosis of cancer using compositions which contain a humanized antibody which specifically binds TAG-72, which is in labeled or unlabeled form.

It is still another object of the invention to provide nucleic acid sequences which encode for humanized antibodies to TAG-72 or fragments thereof. It is a more specific object of the invention to provide nucleic acid sequences which encode humanized antibodies derived from CC49, a murine antibody which specifically binds to TAG-72. It is another object of the invention to provide vectors from which may be expressed humanized antibodies to TAG-72, in particular humanized antibodies derived from CC49, a murine antibody which specifically binds to TAG-72.

BRIEF DESCRIPTION OF THE FIGURES

FIG. 1 aligns amino acid sequences of murine CC49 $V_H$ (SEQ ID NO:1) the NEWM framework regions (SEQ ID NO:2) encoded by the FR starting material, and the humanized NEWM-based $V_H$ (HuVH) (SEQ ID NO:3) disclosed in Example 1. The CDRs are in the boxes. Murine residues retained in the FRs are identified with arrow symbols (↑). Murine FR residues retained in alternate versions of the HuVH (SEQ ID NOS: 4, 5, AND 6) are identified with letter symbols (A), (S), and (K).

FIG. 2 aligns amino acid sequences of murine CC49 $V_K$ (SEQ ID NO:7), the REI framework regions (SEQ ID NO:8) encoded by the FR starting material, and the humanized REI-based $V_K$ (SEQ ID NO:9) disclosed in Example 1. CDRs are in the boxes.

FIG. 3 aligns the variable heavy chain of CC49 (SEQ ID NO:10), the HuCC49 (SEQ ID NO:11) disclosed in Example 1, and NEWM (SEQ ID NO:12).

FIG. 4 aligns the variable light chain of CC49 (SEQ ID NO:13), the HuCC49 (SEQ ID NO:14) disclosed in Example 1, and REI (SEQ ID NO:15).

FIG. 10 is an ELISA showing binding of CC49 antibodies HuVHS/HuVK and HuVH/HuVK to TAG-72.

FIG. 13 presents the single-stranded DNA sequence (SEQ ID NO:16) of the template used to produce the initial humanized NEWM-based VHs, HuVH and HuVHA.

FIG. 14 presents the double-stranded DNA sequence (SEQ ID NO:17) of the template used to produce the alternate humanized VHs, HuVHS and HuVHK.

DETAILED DESCRIPTION OF THE INVENTION

Figure 5:
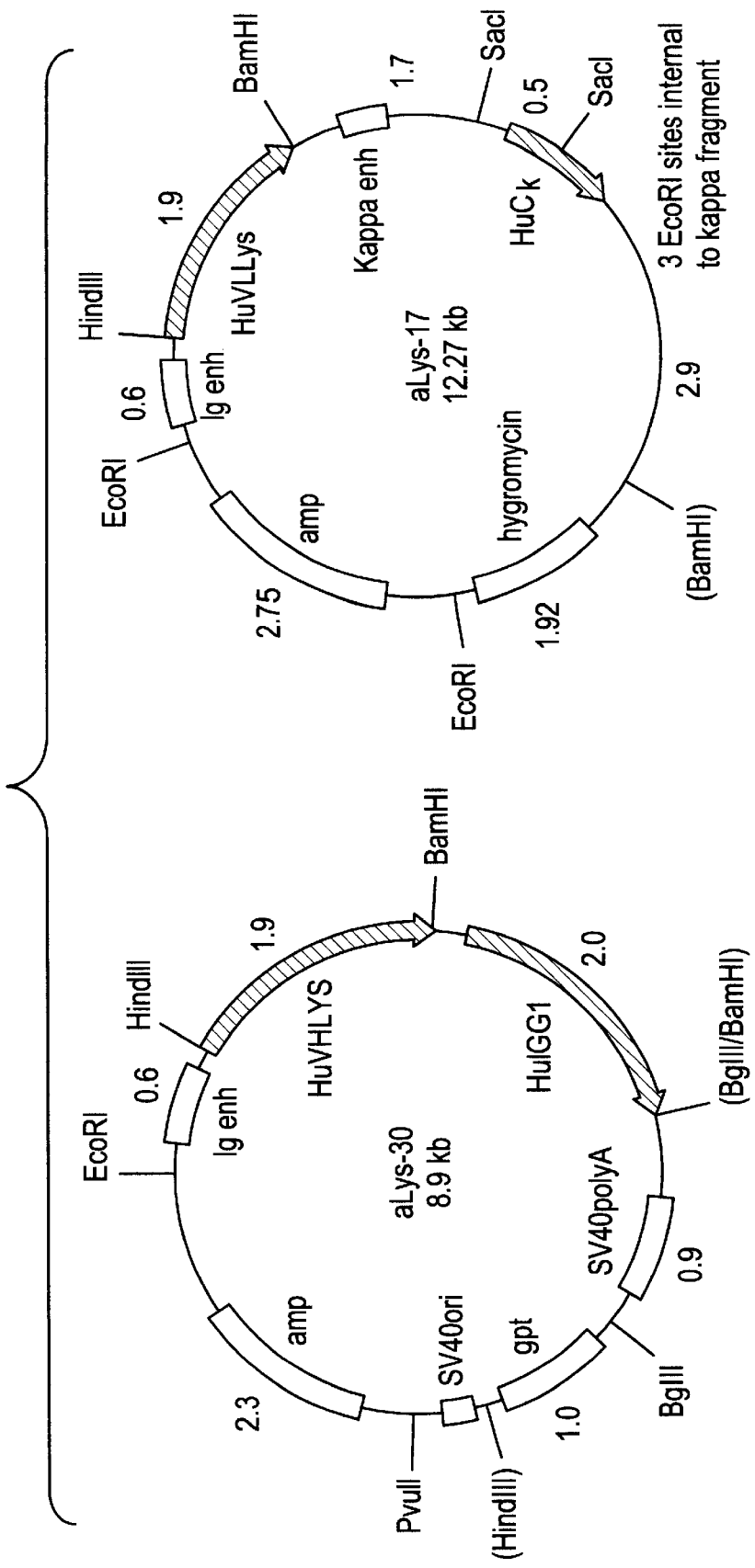
FIG. 5 contains schematics of the vectors used to express the humanized $V_H$ and $V_K$ shown in FIG. 3 and FIG. 4.

Prior to setting forth the invention, definitions of certain terms which are used in this disclosure are set forth below:

Antibody—This refers to single chain, two-chain, and multi-chain proteins and glycoproteins belonging to the classes of polyclonal, monoclonal, chimeric, and hetero immunoglobulins (monoclonal antibodies being preferred);

it also includes synthetic and genetically engineered variants of these immunoglobulins. "Antibody fragment" includes Fab, Fab', F(ab')$_2$, and Fv fragments, as well as any portion of an antibody having specificity toward a desired target epitope or epitopes.

Humanized antibody—This will refer to an antibody derived from a non-human antibody, typically murine, that retains or substantially retains the antigen-binding properties of the parent antibody but which is less immunogenic in humans. This may be achieved by various methods including (a) grafting only the non-human CDRs onto human framework and constant regions with or without retention of critical framework residues, or (b) transplanting the entire non-human variable domains, but "cloaking" them with a human-like section by replacement of surface residues. Such methods as are useful in practicing the present invention include those disclosed in Jones et al., Morrison et al., *Proc. Natl. Acad. Sci. USA*, 81:6851–6855 (1984); Morrison and Oi, *Adv. Immunol.*, 44:65–92 (1988); Verhoeyen et al., *Science*, 239:1534–1536 (1988); Padlan, *Molec. Immun.*, 28:489–498 (1991); Padlan, *Molec. Immun.*, 31(3):169–217 (1994).

Complementarity Determining Region. or CDR—The term CDR, as used herein, refers to amino acid sequences which together define the binding affinity and specificity of the natural Fv region of a native immunoglobulin binding site as delineated by Kabat et al. (1991).

Framework Region—The term FR, as used herein, refers to amino acid sequences interposed between CDRs. These portions of the antibody serve to hold the CDRs in an appropriate orientation for antigen binding. In the antibodies and antibody fragments of the present invention, the framework regions for the light chain variable region may be selected from the group consisting of human lambda light chain FRs and human kappa subgroup I, II, and III light chain FRs, whether comprising their fully human native amino acid sequences or comprising amino acid sequence modifications necessary to retain or increase binding affinity and/or binding specificity.

Constant Region—The portion of the antibody molecule which confers effector functions. In the present invention, murine constant regions are substituted with human constant regions. The constant regions of the subject chimeric or humanized antibodies are derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region chimeric antibodies with desired effector function can be produced.

Preferred constant regions are gamma 1 (IgG1), gamma 3 (IgG3) and gamma 4 (IgG4). More preferred is a constant region of the gamma 1 (IgG1) isotype. The light chain constant region can be of the kappa or lambda type, preferably of the kappa type.

Chimeric antibody—This is an antibody containing sequences derived from two different antibodies, which typically are of different species. Most typically chimeric antibodies comprise human and murine antibody fragments, generally human constant and murine variable regions.

Mammals—Animals that nourish their young with milk secreted by mammary glands, preferably warm blooded mammals, more preferably humans.

Immunogenicity—A measure of the ability of a targeting protein or therapeutic moiety to elicit an immune response (humoral or cellular) when administered to a recipient. The present invention is concerned with the immunogenicity of the subject humanized antibodies or fragments thereof.

Humanized antibody of reduced immunogenicity—This refers to a humanized antibody exhibiting reduced immunogenicity relative to the parent antibody.

Humanized antibody substantially retaining the binding properties of the parent antibody—This refers to a humanized antibody which retains the ability to specifically bind the antigen recognized by the parent antibody used to produce such humanized antibodies. Preferably the humanized antibody will exhibit the same or substantially the same antigen-binding affinity and avidity as the parent antibody, e.g., CC49. Preferably, the affinity of the antibody will at least about 10% of that of the parent antibody. More preferably, the affinity will be at least about 25%, i.e. at least two-fold less than the affinity of the parent antibody. Most preferably the affinity will be at least about 50% that of the parent antibody. Methods for assaying antigen-binding affinity are well known in the art and include half-maximal binding assays, competition assays, and Scatchard analysis. Suitable antigen binding assays are described in this application.

In its broadest embodiment, the present invention is directed to humanized antibodies which specifically bind TAG-72, a pancarcinoma antigen expressed by various human cancers, in particular human colon carcinoma. Preferably, such humanized antibodies will be derived from antibodies having good binding affinity to TAG-72, e.g.: B72.3 (Thor et al., *Cancer Res.*, 46:3118–3127 (1986); Johnson et al., *Cancer Res.*, 46:850–857 (1986)), deposited as ATCC No. HB 8108; CC49 (ATCC No. HB 9459); CC83 (ATCC No. HB 9453); CC46 (ATCC No. HB 9452); CC92 (ATCC No. HB 9454); CC30 (ATCC No. HB 9457); CC11 (ATCC No. 9455); and CC15 (ATCC No. HB 9460); or chimerized forms thereof (see, e.g., EPO 0,365,997 to Mezes et al., The Dow Chemical Company).

Most preferably, such humanized antibodies will be derived from CC49, which has been reported to target human colon carcinoma xenografts efficiently and also to reduce the growth of the xenograft with good efficacy. Molinolo et al., *Cancer Res.*, 50:1291–1298 (1990); Colcher et al., *J. Natl. Cancer Inst.*, 82:1191–1197 (1990).

As discussed above, humanized antibodies afford potential advantages over murine and also chimeric antibodies, e.g., reduced immunogenicity in humans. This is advantageous because it should reduce and potentially eliminate the eliciting of a HAMA response when such humanized antibodies are administered in vivo, e.g., for treatment of cancer or for diagnosis of cancer, e.g., for tumor imaging.

However, as noted, humanization may in some instances adversely affect antigen binding. Preferably, the humanized antibodies of the present invention which specifically bind TAG-72 will possess a binding affinity for TAG-72 of at least about 10% and more preferably at least about 25% and most preferably at least about 50% that of the TAG-72 antigen binding affinity of the parent murine antibody, e.g., B72.3, CC49, CC46, CC30, CC11, CC15, CC83, or another parent antibody. Most preferably, the humanized antibodies of the present invention will possess a binding affinity for TAG-72 of at least about 10% and more preferably at least about 25% and most preferably at least about 50% that of the TAG-72 antigen binding affinity of either CC49 or a chimeric CC49 antibody.

Preferably, the humanized antibodies of the present invention will bind the same epitope as CC49. Such antibodies can be identified based on their ability to compete with CC49 for binding to TAG-72 or to TAG-72-expressing cancer cells.

In general, the subject humanized antibodies are produced by obtaining nucleic acid sequences encoding the variable heavy and variable light sequences of an antibody which binds TAG-72, preferably CC49, identifying the CDRs in said variable heavy and variable light sequences, and grafting such CDR nucleic acid sequences onto human framework nucleic acid sequences.

Preferably, the selected human framework will be one that is expected to be suitable for in vivo administration, i.e., does not exhibit immunogenicity. This can be determined, e.g., by prior experience with in vivo usage of such antibodies and by studies of amino acid sequence similarities. In the latter approach, the amino acid sequences of the framework regions of the antibody to be humanized, e.g., CC49, will be compared to those of known human framework regions, and human framework regions used for CDR grafting will be selected which comprise a size and sequence most similar to that of the parent antibody, e.g., a murine antibody which binds TAG-72. Numerous human framework regions have been isolated and their sequences reported in the literature. See, e.g., Kabat et al., (id.).This enhances the likelihood that the resultant CDR-grafted "humanized" antibody, which contains the CDRs of the parent (e.g., murine) antibody grafted onto the selected human framework regions will significantly retain the antigen binding structure and thus the binding affinity of the parent antibody. As a result of such studies, the FRs of REI and NEWM antibodies have been identified as having amino acid sequences which are likely to allow the CDRs of CC49 to retain a significant degree of antigen binding affinity. As noted, the selected human framework regions will preferably be those that are expected to be suitable for in vivo administration, i.e., not immunogenic. Based on their amino acid sequences, REI and NEWM human framework regions are expected to be substantially non-immunogenic.

Methods for cloning nucleic acid sequences encoding immunoglobulins are well known in the art. Such methods will generally involve the amplification of the immunoglobulin sequences to be cloned using appropriate primers by polymerase chain reaction (PCR). Primers suitable for amplifying immunoglobulin nucleic acid sequences, and specifically murine variable heavy and variable light sequences have been reported in the literature. After such immunoglobulin sequences have been cloned, they will be sequenced by methods well known in the art. This will be effected in order to identify the variable heavy and variable light sequences, and more specifically the portions thereof which constitute the CDRs and FRs. This can be effected by well known methods.

Once the CDRs and FRs of the cloned antibody sequences which are to be humanized have been identified, the amino acid sequences encoding CDRs are then identified (deduced based on the nucleic acid sequences and the genetic code and by comparison to previous antibody sequences) and the corresponding nucleic acid sequences are grafted onto selected human FRs. This may be accomplished by use of appropriate primers and linkers. Methods for selecting suitable primers and linkers to provide for ligation of desired nucleic acid sequences is well within the purview of the ordinary artisan and include those disclosed in U.S. Pat. No. 4,816,397 to Boss et al. and U.S. Pat. No. 5,225,539 to Winter et al.

After the CDRs are grafted onto selected human FRs, the resultant "humanized" variable heavy and variable light sequences will then be expressed to produce a humanized Fv or humanized antibody which binds TAG-72. Typically, the humanized variable heavy and variable light sequences will be expressed as a fusion protein with human constant domain sequences, so that an intact antibody which binds TAG-72 is obtained. However, this is not necessary as the variable heavy and light sequences can also be expressed in the absence of constant sequences to produce a humanized Fv which binds TAG-72. However, fusion of human constant sequences to the humanized variable region(s) is potentially desirable because the resultant humanized antibody which binds TAG-72 will then possess human effector functions such as complement-dependent cytotoxicity (CDC) and antibody-dependent cellular cytotoxicity (ADCC) activity. Such activity has been found in chimeric antibodies, including CC49. The humanized anti-TAG-72 antibodies of the present invention can also support such effector function activity with the added advantage of a greatly decreased risk of a HAMA response.

Methods for synthesizing DNAs encoding a protein of known sequence are well known in the art. Using such methods, DNA sequences which encode the subject humanized $V_L$ and $V_H$ sequences are synthesized, and then expressed in vector systems suitable for expression of recombinant antibodies. This may be effected in any vector system which provides for the subject humanized $V_L$ and $V_H$ sequences to be expressed as a fusion protein with human constant domain sequences and to associate to produce functional (antigen binding) antibodies. Expression vectors and host cells suitable for expression of recombinant antibodies and humanized antibodies in particular, are well known in the art.

The following references are representative of methods and vectors suitable for expression of recombinant immunoglobulins which may be utilized in carrying out the present invention. Weidle et al., *Gene*, 51:21–29 (1987); Dorai et al., *J. Immunol.*, 13(12):4232–4241 (1987); De Waele et al., *Eur. J. Biochem.*, 176:287–295 (1988); Colcher et al., *Cancer Res.*, 49:1738–1745 (1989); Wood et al., *J. Immunol.*, 145(a):3011–3016 (1990); Bulens et al., *Eur. J. Biochem.*, 195:235–242 (1991); Beggington et al., *Biol. Technology*, 10:169 (1992); King et al., *Biochem. J.*, 281:317–323 (1992); Page et al., *Biol. Technology*, 9:64 (1991); King et al., *Biochem. J.*, 290:723–729 (1993); Chaudary et al., *Nature*, 339:394–397 (1989); Jones et al., *Nature*, 321:522–525 (1986); Morrison and Oi, *Adv. Immunol.*, 44:65–92 (1988); Benhar et al., *Proc. Natl. Acad. Sci. USA*, 91:12051–12055 (1994); Singer et al., *J. Immunol.*, 150:2844–2857 (1993); Cooto et al., *Hybridoma*, 13(3):215–219 (1994); Queen et al., *Proc. Natl. Acad. Sci. USA*, 86:10029–10033 (1989); Caron et al., *Cancer Res.*, 32:6761–6767 (1992); Cotoma et al., *J. Immunol. Meth.*, 152:89–109 (1992). Moreover, vectors suitable for expression of recombinant antibodies are commercially available. The vector may, e.g., be a bare nucleic acid segment, a carrier-associated nucleic acid segment, a nucleoprotein, a plasmid, a virus, a viroid, or a transposable element.

Host cells known to be capable of expressing functional immunoglobulins include, e.g.: mammalian cells such as Chinese Hamster Ovary (CHO) cells; COS cells; myeloma cells, such as NSO and SP2/0 cells; bacteria such as *Escherichia coli*; yeast cells such as *Saccharomyces cerevisiae*; and other host cells. Of these, CHO cells are used by many researchers given their ability to effectively express and secrete immunoglobulins. NSO cells are one of the preferred types of host cells useful in the present invention.

Essentially, recombinant expression of humanized antibodies is effected by one of two general methods. In the first method, the host cells are transfected with a single vector which provides for the expression of both heavy and light variable sequences optionally fused to selected constant regions. In the second method, host cells are transfected with two vectors, each of which encodes a different variable chain (i.e. a variable heavy chain or variable light chain); each variable chain-encoding vector may optionally provide for the expression of the variable chain fused to a selected constant region.

Human constant domain sequences are well known in the art, and have been reported in the literature. Preferred human light chain constant sequences include the kappa and lambda constant light sequences. Preferred human heavy constant sequences include human gamma 1, human gamma 2, human gamma 3, human gamma 4, and mutated versions thereof which provide for altered effect or function, e.g., enhanced in vivo half-life or reduced Fc receptor binding.

After expression, the antigen binding affinity of the resulting humanized antibody will be assayed by known methods, e.g., Scatchard analysis. In a particularly preferred embodiment, the antigen-binding affinity of the humanized antibody will be at least 25% of that of the parent antibody, e.g., CC49, i.e. a minimum of two-fold less than that of native or chimeric CC49. Most preferably, the affinity of the humanized antibody will be at least about 50% of that of the parent antibody, e.g., CC49.

In some instances, humanized antibodies produced by grafting CDRs (from an antibody which binds TAG-72) onto selected human framework regions may provide humanized antibodies having the desired affinity to TAG-72. However, it may be necessary or desirable to further modify specific residues of the selected human framework in order to enhance antigen binding. This may occur because it is believed that some framework residues are essential to or at least affect antigen binding. Preferably, those framework residues of the parent (e.g., murine) antibody which maintain or affect combining-site structures will be retained. These residues may be identified by X-ray crystallography of the parent antibody or Fab fragment, thereby identifying the three-dimensional structure of the antigen-binding site. Also, framework residues involved in antigen binding may potentially be identified based on previously reported humanized murine antibody sequences. Thus, it may be beneficial to retain such framework residues or others from the parent murine antibody to optimize TAG-72 binding. Preferably, such methodology will confer a "human-like" character to the resultant humanized antibody thus rendering it less immunogenic while retaining the interior and contacting residues which affect antigen-binding.

The present invention further embraces variants and equivalents which are substantially homologous to the humanized antibodies and antibody fragments set forth herein. These may contain, e.g., conservative substitution mutations, i.e. the substitution of one or more amino acids by similar amino acids. For example, conservative substitution refers to the substitution of an amino acid with another within the same general class, e.g., one acidic amino acid with another acidic amino acid, one basic amino acid with another basic amino acid, or one neutral amino acid by another neutral amino acid. What is intended by a conservative amino acid substitution is well known in the art.

The phrase "substantially homologous" is used in regard to the similarity of a subject amino acid sequence (of an oligo- or poly-peptide or protein) to a related, reference amino acid sequence. This phrase is defined as at least about 75% Correspondence, i.e. the state of identical amino acid residues being situated in parallel, between the subject and reference sequences when those sequences are in "alignment," i.e. when a minimal number of "null" bases have been inserted in the subject and/or reference sequences so as to maximize the number of existing bases in correspondence between the sequences. "Null" bases are not part of the subject and reference sequences; also, the minimal number of "null" bases inserted in the subject sequence may differ from the minimal number inserted in the reference sequence. In this definition, a reference sequence is considered "related" to a subject sequence where both amino acid sequences make up proteins or portions of proteins which are either αTAG-72 antibodies or antibody fragments with αTAG-72 binding affinity. Each of the proteins comprising these αTAG-72 antibodies or antibody fragments may independently be antibodies or antibody fragments or hi- or multi-functional proteins, e.g., such as fusion proteins, bi- and multi-specific antibodies, single chain antibodies, and the like.

The present invention is further directed to nucleic acid sequences from such humanized antibodies may be expressed, as well as expression vectors which provide for the production of such humanized antibodies in transformed host cells.

In the preferred embodiments, such humanized antibodies and corresponding nucleic acid sequences will be derived from CC49. Most preferably, the humanized heavy chains will have the amino acid sequences set forth in FIG. 1 or 3 and the humanized light chains will have the amino acid sequences set forth in FIG. 2 or 4. However, as discussed, the invention further contemplates other modifications of these humanized variable heavy and light sequences, e.g., sequences which further comprise one or more conservative amino acid substitutions or sequences which retain one or more additional murine framework residues which affect (enhance) antigen binding, which are alternatives to or supplements for those already shown in these Figures.

The subject humanized antibodies, because they specifically bind TAG-72, a pancarcinoma antigen expressed on many different cancer cell types (e.g., colon carcinoma, breast carcinoma, ovarian carcinoma, prostate carcinoma), and further because they are expected to be significantly non-immunogenic in humans, should be suitable for use as therapeutics for the treatment or prevention of cancers characterized by TAG-72 expression, and as diagnostic agents, e.g., for use in tumor imaging or in the RIGS system (Radioimmunoguided Surgery system of Neoprobe Corp., Dublin, Ohio). See Hinkle et al, Antibody, *Immunoconjugates and Radiopharmaceuticals*, 4(3):339–358 (1991). One skilled in the art would be able, by routine experimentation, to determine what an effective, non-toxic amount of antibody would be for the purpose of treating cancer. Generally, however, an effective dosage will be in the range of about 0.05 to 100 milligrams per kilogram body weight per day.

The antibodies of the invention may be administered to a mammal in accordance with the aforementioned methods of treatment in an amount sufficient to produce such effect to a therapeutic, prophylactic, or diagnostic effect. Such antibodies of the invention can be administered to such mammal in a conventional dosage form prepared by combining the antibody of the invention with a conventional pharmaceutically acceptable carrier or vehicle, diluent, and/or excipient according to known techniques to form a suspension, injectable solution, or other formulation. It will be recognized by one of skill in the art that the form and character of the pharmaceutically acceptable carrier or diluent is dictated by the amount of active ingredient with which it is to be combined, the route of administration and other well-known variables.

Pharmaceutically acceptable formulations may include, e.g., a suitable solvent, preservatives such as benzyl alcohol if desired, and a buffer. Useful solvent may include, e.g., water, aqueous alcohols, glycols, and phsophonate and carbonate esters. Such aqueous solutions contain no more than 50% by volume of organic solvent. Suspension-type formulations may include a liquid suspending medium as a carrier, e.g., aqueous polyvinylpyrrolidone, inert oils such as vegetable oils or highly refined mineral oils, or aqueous cellulose ethers such as aqueous carboxymethylcellulose. A thickener such as gelatin or an alginate may also be present, one or more natural or synthetic surfactants or antifoam agents may be used, and one or more suspending agents such as sorbitol or another sugar may be employed therein. Such formations may contain one or more adjuvants.

The route of administration of the antibody (or fragment thereof) of the invention may be oral, parenteral, by inhalation or topical. The term parenteral as used herein includes intravenous, intramuscular, subcutaneous, rectal, vaginal or intraperitoneal administration. The subcutaneous, intravenous and intramuscular forms of parenteral administration are generally preferred. The daily parenteral and oral dosage regimens for employing humanized antibodies of the invention prophylactically or therapeutically will generally be in the range of about 0.005 to 100, but preferably about 0.5 to 10, milligrams per kilogram body weight per day.

The antibody of the invention may also be administered by inhalation. By "inhalation" is meant intranasal and oral inhalation administration. Appropriate dosage forms for such administration, such as an aerosol formulation or a metered dose inhaler, may be prepared by conventional techniques. The preferred dosage amount of a compound of the invention to be employed is generally within the range of about 0.1 to 1000 milligrams, preferably about 10 to 100 milligrams/kilogram body weight.

The antibody of the invention may also be administered topically. By topical administration is meant non-systemic administration. This includes the administration of a humanized antibody (or humanized antibody fragment) formulation of the invention externally to the epidermis or to the buccal cavity, and instillation of such an antibody into the ear, eye, or nose, and wherever it does not significantly enter the bloodstream. By systemic administration is meant oral, intravenous, intraperitoneal, subcutaneous, and intramuscular administration. The amount of an antibody required for therapeutic, prophylactic, or diagnostic effect will, of course, vary with the antibody chosen, the nature and severity of the condition being treated and the animal undergoing treatment, and is ultimately at the discretion of the physician. A suitable topical dose of an antibody of the invention will generally be within the range of about 1 to 100 milligrams per kilogram body weight daily.

Formulations

While it is possible for an antibody or fragment thereof to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation. The topical formulations of the present invention, comprise an active ingredient together with one or more acceptable carrier(s) therefor and optionally any other therapeutic ingredients(s). The carrier (s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Kits according to the present invention include frozen or lyophilized humanized antibodies or humanized antibody fragments to be reconstituted, respectively, by thawing (optionally followed by further dilution) or by suspension in a (preferably buffered) liquid vehicle. The kits may also include buffer and/or excipient solutions (in liquid or frozen form)—or buffer and/or excipient powder preparations to be reconstituted with water—for the purpose of mixing with the humanized antibodies or humanized antibody fragments to produce a formulation suitable for administration. Thus, preferably the kits containing the humanized antibodies or humanized antibody fragments are frozen, lyophilized, pre-diluted, or pre-mixed at such a concentration that the addition of a predetermined amount of heat, of water, or of a solution provided in the kit will result in a formulation of sufficient concentration and pH as to be effective for in vivo or in vitro use in the treatment or diagnosis of cancer. Preferably, such a kit will also comprise instructions for reconstituting and using the humanized antibody or humanized antibody fragment composition to treat or detect cancer. The kit may also comprise two or more component parts for the reconstituted active composition. For example, a second component part—in addition to the humanized antibodies or humanized antibody fragments—may be bifunctional chelant, bifunctional chelate, or a therapeutic agent such as a radionuclide, which when mixed with the humanized antibodies or humanized antibody fragments forms a conjugated system therewith. The above-noted buffers, excipients, and other component parts can be sold separately or together with the kit.

It will be recognized by one of skill in the art that the optimal quantity and spacing of individual dosages of a humanized antibody or humanized antibody fragment of the invention will be determined by the nature and extent of the condition being treated, the form, route and site of administration, and the particular animal being treated, and that such optima can be determined by conventional techniques. It will also be appreciated by one of skill in the art that the optimal course of treatment, i.e., the number of doses of an antibody or fragment thereof of the invention given per day for a defined number of days, can be ascertained by those skilled in the art using conventional course of treatment determination tests.

The subject humanized antibodies may also be administered in combination with other anti-cancer agents, e.g., other antibodies or drugs. Also, the subject humanized antibodies or fragments may be directly or indirectly attached to effector having therapeutic activity. Suitable effector moieties include by way of example cytokines (IL-2, TNF, interferons, colony stimulating factors, IL-1, etc.), cytotoxins (Pseudomonas exotoxin, ricin, abrin, etc.), radionuclides, such as $^{90}Y$, $^{131}I$, $^{99m}Tc$, $^{111}In$, $^{125}I$, among others, drugs (methotrexate, daunorubicin, doxorubicin, etc.), immunomodulators, therapeutic enzymes (e.g., beta-galactosidase), anti-proliferative agents, etc. The attachment of antibodies to desired effectors is well known. See, e.g., U.S. Pat. No. 5,435,990 to Cheng et al. Moreover, bifunctional linkers for facilitating such attachment are well known and widely available. Also, chelators (chelants and chelates) providing for attachment of radionuclides are well known and available.

Alternatively, the subject humanized antibodies or fragments specific to TAG-72 may be used as immunodiagnostic agents both in vivo and in vitro. A particularly preferred usage is for in vivo imaging of cancer cell lesions which express TAG-72. The subject antibodies are preferred because they should elicit no significant HAMA or allergic response. Thus, they may be used repeatedly to monitor the disease status of a patient.

As noted above, another preferred application of the subject humanized antibodies or fragments thereof is in the RIGS system (Radioimmunoguided Surgery system of Neoprobe Corp., Dublin, Ohio). This technique, also known as the RIGS system involves the intravenous administration of a radiolabeled monoclonal antibody or its fragment prior to surgery. After allowing for tumor uptake and blood clearance of radioactivity, the patient is taken to the operating room where surgical exploration is effected with the aid of a hand-held gamma activity probe, e.g., NEOPROBE 1000 (Neoprobe Corp., Dublin, Ohio). This helps the surgeon identify the tumor metastases and improve the complications of excision. The RIGS system (Radioimmunoguided Surgery system of Neoprobe Corp., Dublin, Ohio) is advantageous because it allows for the detection of tumors not otherwise detectable by visual inspection and/or palpation.

See, O'Dwyer et al, *Arch. Surg.*, 121:1 391–1394 (1986). This technique is described in detail in Hinkle et al, Antibody, *Immunoconjugates and Radiopharmacouticals*, 4:(3)339–358 (1991) (citing numerous references describing this technique). This reference also discloses the use of this technique with the CC49 monoclonal antibody itself. This technique is particularly useful for cancers of the colon, breast, pancreas, and ovaries.

The subject humanized antibodies or humanized antibody fragments thereof radiolabeled with radionuclides which are suitable for in vivo administration, e.g., iodine radionuclides such as $^{131}I$ and $^{125}I$; $^{111}In$ and $^{99m}Tc$ are also suitable radiolabels.

The subject humanized antibodies may be used alone or in combination with other antibodies. Also, the subject humanized antibodies may be prepared in the form of a diagnostically effective composition. Generally, this will entail the incorporation of diagnostically acceptable carriers and excipients, and labels which provide for detection. Suitable labels include diagnostic radionuclides, enzymes, etc. Methods for using antibodies for tumor imaging are well known in the art.

Without further elaboration, it is believed that one skilled in the art can, using the preceding description, utilize the present invention to its fullest extent. The invention will be further clarified by a consideration of the following examples, which are intended to be purely exemplary of the present invention are thus to be construed as merely illustrative examples and not limitations of the scope of the present invention in any way.

EXAMPLES

Materials and Methods

DNA Template Preparation

All recombination work was performed upon DNA sequences in plasmid M13 vectors. The source of the NEWM framework regions for producing the initial humanized CC49 $V_H$ was an M13 construct bearing, between the M13 BamHI and HindIII sites a DNA segment having the nucleotide sequence shown in FIG. 13. The source of REI framework regions for producing the initial humanized CC49 VL was an M13 construct bearing—between the M13 BamHI and HindIII sites—a DNA segment encoding the REI amino acid sequence of FIG. 2.

When overlap-extension procedures were used to introduce mutations into a given DNA sequence, double stranded M13 DNA was utilized. In contrast, when extension-ligation procedures were used instead, the oligonucleotides were designed to anneal to only one of the two DNA strands. In this latter procedure, the M13 DNA was first treated to substitute uridine for every thymidine base in the DNA, to produce uridinylated DNA. This was accomplished by transfecting the M13 plasmid DNA into competent cells lacking dUTPase and uracil glycosylase, normally RZ1032 cells (though CJ236 cells available from Bio-Rad of Hercules, Calif., are also suitable) by combining the following ingredients.

1 µL of M13 plasmid DNA 4 mL of LB broth

40 µL of competent RZ1032 cells.

The culture was shaken for 5 hours at 37° C. and the resulting single-stranded plasmid DNA (ssDNA) was isolated and dissolved in 50 µL Tris-EDTA buffer. The DNA was then treated with uracil glycosylase by mixing together:

1 μL uridinylated ssDNA

1 μL 10×glycosylase buffer

1 U uracil glycosylase (Gibco BRL, Gathersburg, Md.)

40 μL 25 mM MgCl2.

This mixture was then incubated at 37° C. for one hour and then 6.6 μL 25 mM MgCl2 and 9.9 μL 1M NaOH. The mixture was then further incubated for 5 minutes at 37° C. and 16.5 μL of 0.6M HCl was then added to neutralize the mixture. The DNA was then ethanol precipitated and dissolved in water.

M13 Oligonucleotide Primers

The following oligonucleotide primers were used throughout the process of preparing the humanized CC49 VHs and VLs exemplified below.

10. 5'-CTAAAACGACGGCCAGT-3' (SEQ ID NO:18);

11. 5'-AACAGCTATGACCATG-3' (SEQ ID NO:19);

385. 5'-GCGGGCCTCTTCGCTATTACGC-3' (SEQ ID NO:20); and 391. 5'-CTCTCTCAGGGCCAGGCGGTGA-3' (SEQ ID NO:21).

These primers are complementary to regions of the plasmid M13 which are external both to the (NEWM or REI) target framework sequences and to the BamHI site-to-HindIII site section of M13.

Murine Variable-Regions

In order to compare the antibody binding characteristics of the antibodies produced according to the examples set forth below, antibodies having a chimeric heavy chain (i.e. a heavy chain having a murine CC49 VH region and a human IgG1 constant region) and/or a chimeric light chain (i.e. a light chain having a murine CC49 VL and a human κ constant region) were expressed. The source of these chimeric chains was the ATCC-deposited cell line HB9884 (Budapest) which expresses a chimeric CC49 antibody having both chains. The heavy chain of this antibody was termed "MuVH" and the light chain thereof was termed "MuVL."

Oligonucleotide Phosphorylation Protocol

Mutating oligonucleotides used in non-overlap extensions were phosphorylated according to the procedure below. In a final volume of 25 μL, the following ingredients were combined:

10 pmol of each oligonucleotide,

5 μL of a 5×polynucleotide kinase buffer, and

5 U of T4 polynucleotide kinase (Gibco BRL).

The phosphorylation reaction was started with the addition of the enzyme and allowed to proceed for one hour at 37° C.

Annealing Protocol for Non-Overlap Extension-ligations

The annealing step for non-overlap extension-ligations involved performing one annealing in which all mutation-carrying oligonucleotides and one primer oligonucleotide were annealed to a single stranded DNA template in which all thymidine bases had been replaced with uridine bases. The mutating oligonucleotides were first phosphorylated according to the above oligonucleotide phosphorylation protocol. In a final volume of 20 μL, the following ingredients were combined:

1 pmol of each mutation-carrying phosphorylated oligonucleotide 1 pmol of a primer oligonucleotide 4 μL 5×annealing buffer 0.2 pmol ssU-DNA template.

The mixture was then heated to 90° C. for 30 sec., then quickly cooled to 70° C., and finally allowed to slowly cool to 37° C.

Extension-ligation Protocol for Non-overlap Extension-ligations

After completion of the annealing step in which the primer and phosphorylated mutating oligonucleotides were annealed to the ssU-DNA template, extension-ligation was performed as follows. In a final volume of 30 μL, the following ingredients were combined:

20 μL annealed ssU-DNA (i.e. the contents of the above annealing procedure)

2 μL 5×annealing buffer

2 μL 0.1 M dithiothreitol 0.3 μL 0.1M ATP

1 μL 6.25 mM dNTP mixture of equimolar amounts of dATP, dTTP, dGTP, dCTP 2.5 U T7 DNA polymerase (USB, now Amersham Life Sciences, Cleveland, Ohio)

0.5 U T4 DNA ligase (Gibco BRL)

Water to 30 μL.

This mixture was then incubated at room temperature for 1 hour.

Standard PCR Protocols

The following procedure was used, alternately, both to amplify the non-overlap extension-ligation DNA sequences and to perform extension of each overlap DNA sequence. In a final volume of 50 μL, the following ingredients were combined:

2 μL template DNA (either annealed ssU-DNA or non-annealed ssDNA)

5 μL 10×Vent buffer (NEB, i.e. New England Biolabs, Beverly, Mass.) or 10×Thermalase buffer (IBI of New Haven, Conn.)

2 μL 6.25 mM dNTP mixture of equimolar amounts of dATP, dTTP, dGTP, dCTP 25 pmol of one oligonucleotide primer 25 pmol of either a mutation-carrying oligonucleotide (for overlap-extension) or a second oligonucleotide primer 1 U Vent DNA polymerase (NEB) or Thermalase DNA polymerase (IBI).

Reactions were initiated with the addition of the DNA polymerase and then treated with about 15 cycles of: (1) 94° C. for 30 sec., (2) 50° C. for 30 sec., and (3) 30–60 seconds at either 75° C. (for Vent DNA polymerase) or 72° C. (for Thermalase). Reactions were brought to completion with 5 minutes at a constant temperature of either 75° C. For Vent DNA polymerase) or 72° C. (for Thermalase).

PCR Overlap-extension Amplification Protocol

After a pair of PCR reactions were performed—one for each of the two (partially complementary) overlapping DNA segments—the two resulting segments were joined according to the following PCR procedure. In a final volume of 50 μL, the following ingredients were mixed:

1 μL of each overlap DNA (from the above overlap PCR extension reactions)

5 μL 10×Vent buffer (NEB) or Thermalase buffer (IBI)

2 μL 6.25 mM dNTP mixture of equimolar amounts of dATP, dTTP, dGTP, dCTP 25 pmol of each oligonucleotide primer used in the overlap PCR extensions 1 U Vent DNA polymerase (NEB) or Thermalase DNA polymerase (IBI).

Reactions were initiated with the addition of the DNA polymerase and then treated with about 15 cycles of: (1) 94° C. for 30 sec., (2) 50° C. for 30 sec., and (3) 30–60 seconds at either 75° C. (for Vent DNA polymerase) or 72° C. (for Thermalase). Reactions were brought to completion with 5 minutes at a constant temperature of either 75° C. (for Vent DNA polymerase) or 72° C. (for Thermalase).

Transfer of Humanized CC49 Variable Region DNA Sequences from M13 to pSV Vectors and Subsequent Antibody Expression Humanized antibodies were expressed in pSV vectors grown in NSO cells. The humanized variable region constructs which were produced in the plasmid, M13, were digested with 10 U each of HindIII and BamHI (both from BRL, i.e. Gibco BRL) for 1 hour at 37° C. in a final volume of 100 µL with Tris-EDTA buffer. The resulting DNA fragments were then run on a low melting point agarose gel, the band containing the humanized construct DNA was cut out, and the DNA was purified using an ELUTIP 'd' column with 20 µL Tris-EDTA buffer. 10 µL of the purified DNA preparation was then combined with 1 µL of a HindIII and BamHI-digested pSV preparation, 3 µL of 5× ligase buffer, and 1 U of T4 DNA ligase (BRL), in order to insert the construct into a pSV plasmid. Humanized CC49 VH constructs were inserted into pSVgpt vectors bearing a human IgG1 heavy chain constant region; the pSVgpt vector used is the "aLYS-30" shown in FIG. 5. Humanized CC49 VL constructs were inserted into pSVhyg vectors bearing a human κ light chain constant domain; the pSVhyg vector used in the "aLys-17" shown in FIG. 5. Each humanized variable region construct was inserted adjacent to the respective constant region, i.e. so as to replace either the HuVHLYS or the HuVLLys segment illustrated in FIG. 5.

The resulting vectors were transfected into NSO cells as follows. About 3 µg of the VH vector, or about 6 µg of the VL vector, produced by the pSV-insertion procedures, was then linearized by digestion with 10 U PvuI (Gibco BRL). The digested DNA was then precipitated with ethanol and redissolved in 50 µL of water. NSO cells were collected by centrifugation and resuspended in 0.5 mL Dulbecco's Modified Eagle's Medium (DMEM) and then transferred to a Gene Pulser cuvette (Bio-Rad). The DNA from both one VH and one VL construct was gently mixed with the cells by pipetting and the cuvette was left on ice for 5 minutes. Next, the cuvette was inserted between the electrodes of the Bio-Rad Gene Pulser and a single pulse of 170V at 960 µF was applied. The contents of the cuvette were then transferred to a flask containing 20 mL DMEM and the cells were allowed to rest for 1–2 days at 37° C. Cells were again harvested by centrifugation and resuspended in 36 mL selective DMEM. 1.5 mL aliquots of this resuspension were placed in each well of a 24-well plate and incubated at 37° C. for 4 days, at which time the medium in each well was replaced with 1.5 mL of fresh selective DMEM. After 6 more days of incubation at 37° C., surviving cell colonies were visible to the naked eye and the supernatants of each well were assayed for antibody production. Both whole antibody production (i.e. without purification) and purified antibody production were assayed. To obtain purified antibodies, the supernatants were passed through a protein A column.

ELISA Assay Protocols

Antibody concentrations and antibody binding characteristics were tested using enzyme-linked immunosorbent assay (ELISA) procedures which are set forth as follows.

Measurement of IgG Concentration

The concentration of IgG secreted from transfected cells was measured using an enzyme-linked immunosorbent assay (ELISA) procedure which is set forth as follows.

Polyvinyl chloride (PVC) microtiter plates (Dynatech Laboratories, Chantilly, Va., catalog # 001-010-2101) were coated with goat anti-human IgG (0 mg/mL, GAHIG, Southern Biotechnology Associates, Inc., Birmingham, Ala., catalog # 2010-01) diluted with Milli-Q® water and placed on the plates using 50 mL/well. Plates were air-dried overnight at ambient temperature or at 37° C. for 3 hours. Prior to use, non-specific binding was blocked the addition of 0.2 mL/well of 1% (w/v) bovine serum albumin (Sigma, St. Louis, Mo. catalog # A7888) in phosphate buffered saline (Sigma, catalog # 1000-3) (PBS/BSA). All incubations were carried out in a humidified container. Plates were incubated for 1–2 hours at 37° C. and the blocking solution removed prior to sample addition. Two-fold serial dilutions of samples or a standard IgG solution set at 500 ng/mL (50 µL/well) were made in triplicate in the PBS/BSA solution. The plate was incubated at 37° C. for 3 hours or overnight at 4° C. The plate was washed 3 times with 0.025% Tween-20 (v/v, Sigma) using an automatic plate washer. 50 µL/well of 1:1000 dilution of a goat anti-human IgG conjugated to Horseradish Peroxidase (Southern Biotechnology Associates Inc.) was added and incubated at 37° C. for 1.5 hours. The wells were washed 3 times with 0.025% Tween-20 (v/v, Sigma) using an automatic plate washer and 50 µL/well OPD substrate buffer added. The color was developed for 4 minutes, stopped with 12.5 µL 12.5% $H_2SO_4$ and the absorbance at 492 nm read. The concentration of IgG in the test sample was estimated by comparison of the mean of the optical densities to a standard curve constructed from the standard IgG.

Determination of Relative Affinities of Humanized Antibodies

Antibody binding characteristics were tested in an ELISA using partially purified TAG-72 antigen immobilized on Polyvinyl chloride (PVC) microtiter plates (Dynatech Laboratories, Chantilly, Va., catalog# 001-010-2101)

PVC plates were coated with 50 µL/well TAG-72 (Dow Chemical, lot #040191), diluted 1:300 in Milli-Q water. Plates were air-dried overnight at ambient temperature or at 37° C. for 3 hours. Prior to use, non-specific binding was blocked the addition of 0.2 mL/well of 1% (w/v) bovine serum albumin (Sigma, St. Louis, Mo. catalog # A7888) in phosphate buffered saline (Sigma, catalog # 1000-3) (PBS/BSA). Plates were incubated for 1–2 hours at 37° C. and the blocking solution removed prior to sample addition. All incubations were carried out in a humidified container. Two-fold serial dilutions (starting concentration range of 1.0 g/ml–10 µg/ml) of the samples to be tested in the PBS/BSA solution were added to triplicate wells of the TAG-coated plate (50 µL/well). The plate was incubated overnight at 4° C. or 1–2 hours at 37° C. The plate was washed 3-times with 0.025% Tween-20 (v/v, Sigma) using an automatic plate washer. 50 µL/well of 1:1000 dilution of a goat anti-human IgG conjugated to Horseradish Peroxidase (Southern Biotechnology Associates Inc.) was added and incubated at 37° C. for 1.5 hours. The wells were washed 3 times with 0.025% Tween-20 (v/v, Sigma) using an automatic plate washer and 50 µL/well OPD substrate buffer added. The color was developed for 4 minutes, stopped with 12.5 µL 12.5% $H_2SO_4$ and the absorbance at 492 nm read.

Determination of Affinity Constants for Binding to TAG-72

Two-fold dilutions of purified Hu-CC49 were prepared in PBS/BSA over a range of 1.0 µg/ml–0.003 µg/ml and samples (20 uL/well) were applied in triplicate to TAG coated PVC prepared and blocked as described supra. Plates were incubated overnight at 4° C. Following this incubation, samples were transferred from the plate to the corresponding wells on the GAHIG-coated trap plate. The original TAG plate was washed 3-times with 0.025% Tween-20 (v/v, Sigma, catalog # P1379) using an automatic plate washer. An $^{125}$I-labeled goat anti-human IgG probe (ICN Biomedicals, Inc., catalog #68088) was diluted to 75,000 cpm/25μL in PBS/BSA and added (25 μL/well) to all wells. This TAG plate was incubated for 1 hour at 37° C.

After a 1 hour incubation at 37° C., the trap plate was washed as described above and $^{125}$I-labeled GAHIG probe was added. This plate was incubated for 1 hour at 37° C. Both plates (TAG and GAHIG-trap) containing probe were then washed with a microplate washer to remove the unbound probe. A plate cutter (D. Lee, Sunnyvale, Calif., Model HWC-4) was used to separate the wells from the plate frame. The radioactivity in each well was quantified by a gamma counter. The resulting data was analyzed according to the method of Scatchard (*Ann. NY Acad.*, 51:600–672 (1946)).

Example 1

Preparation of CDR-grafted (Initial Humanized) Antibody From Murine CC49

We describe in this Example the construction of humanized CC49 Mabs (CC49 HuVH/HuVK) using the $V_L$ and $V_H$ frameworks of human Mabs REI and NEWM, respectively. The CDRs for murine CC49 were grafted onto human frameworks according to known methods as discussed supra. In particular, human frameworks were selected from antibodies which, based on previous studies, were predicted to be suitable, i.e. which should not adversely affect antigen binding and not exhibit significant immunogenicity in humans. The human frameworks selected for the variable heavy and variable light chains, respectively, were NEWM and REI. In the production of the initial version of the humanized VH, certain murine framework residues were also retained which, based on previous studies, might allow retention of antigen binding properties. Specifically, residues Y27, T30, A72, F95, and T97 of the murine heavy chain were initially retained. Concurrently, an alternate version of the humanized VH was produced which retained, in addition, the murine framework residue A24.

The production of these NEWM-grafted humanized CC49 VHs was accomplished according to the annealing and extension-ligation protocols described above, using a single-stranded M13 DNA template bearing, between the HindIII and BamHI sites thereof, a DNA segment having the nucleotide sequence shown in FIG. 13. In this procedure, Primer 11 was used in conjunction with a set of mutating oligonucleotides. These mutating oligonucleotides were designed and synthesized with the following sequences:

1 a. 5'-GCTGTCTCACCCAGTGAATTGCATGGTCAGT-GAAGGTGTAGCCAGA CACGGTGCAGGTCA-3' (SEQ ID NO:22);

1 b. 5'-GCTGTCTCACCCAGTGAATTGCATGGTCAGT-GAAGGTGTAGCCAGA CGCGGTGCAGGTCA-3' (SEQ ID NO:23);

2. 5'-CTGGTGTCTGCCAGCATTGTCACTCTCCCCT-TGAACCTCTCATTGTAT TTAAAATCATCATTTC-CGGG AGAAAAATATCCAATCCACTCAAGAC-3' (SEQ ID NO:24); and 3. 5'-GGACCCTTGGCCCCAGTAGGCCATATTCAG-GGATCTTGTACAGAAAT AGACCGCGGTGTC-3' (SEQ ID NO:25)

Codons which were designed into the oligonucleotides in order to retain murine FR amino acids are shown in bold-face type. After extension-ligation, amplifying PCR was performed using the standard PCR protocol with Vent DNA polymerase. The use of two versions of mutating oligonucleotide 1 resulted in the formation of two initial humanized $V_H$s. These were named "CC49 NMVH," also called "HuVH," (for constructs incorporating oligonucleotide 1) and "HuVHA" (for constructs incorporating oligonucleotide 1b).

In the production of the initial version of the humanized VL, no uniquely murine framework residues were retained. The production of the REI-grafted humanized CC49 V, was accomplished according to the annealing and extension-ligation protocols described above, using a ssM13 template bearing, between the HindIII and BamHI sites thereof, a ssU-DNA segment encoding the REIVK sequence shown in FIG. 2. In this procedure, Primer 385 was used in conjunction with a set of mutating oligonucleotides. These mutating oligonucleotides were designed and synthesized with the following sequences:

21. 5'-GTTCTTCTGATTACCACTGTATAAAAGACTT-TGACTGGAC-3' (SEQ ID NO:26);

22. 5'-CAGATTCCCTAGCGGATGCCCAGTAG-3' (SEQ ID NO:27);

23. 5'-TTCTACTCACGTGTGATTTGCAGCTTGGTCC-CTTGGCCGAACGTGAG GGGATAGGAATAGTA-TTGCTGGCAGTAGTAG-3' (SEQ ID NO:28); and 24. 5'-GCTCTGGGTCATCTGGATGTCGG-3' (SEQ ID NO:29).

After extension-ligation, amplifying PCR was performed using the Thermalase standard PCR protocol described above. The resulting humanized $V_L$ was named "CC49 REVK" and was also called "HuVK."

The two heavy chain constructs, HuVH and HuVHA, and the light chain construct, HuVH, which were situated in M13 vectors, were grown and expressed in TG1 cells. The polypeptide expression products of these constructs were sequenced and the amino acid sequences of these constructs are presented in FIGS. 1 and 2.

These DNA constructs were then inserted into pSV expression vectors as described above. Combinations of these with each other or with the ATCC (Budapest) HB 9884 DNA sequences encoding the chimeric MuVH or MuVL were then inserted into NSO cells. Specifically, the following four combinations of heavy and light chain constructs were separately transfected into NSO cells as described above: HuVHA and MuVK, HuVHA and HuVK, MuVH and MuVK, and HuVH and HuVK. These combinations were expressed and the resulting antibodies were then tested for antigen binding characteristics using the ELISA assay set forth above. The results of these assays are shown in FIGS. 6–9.

Figure 6:
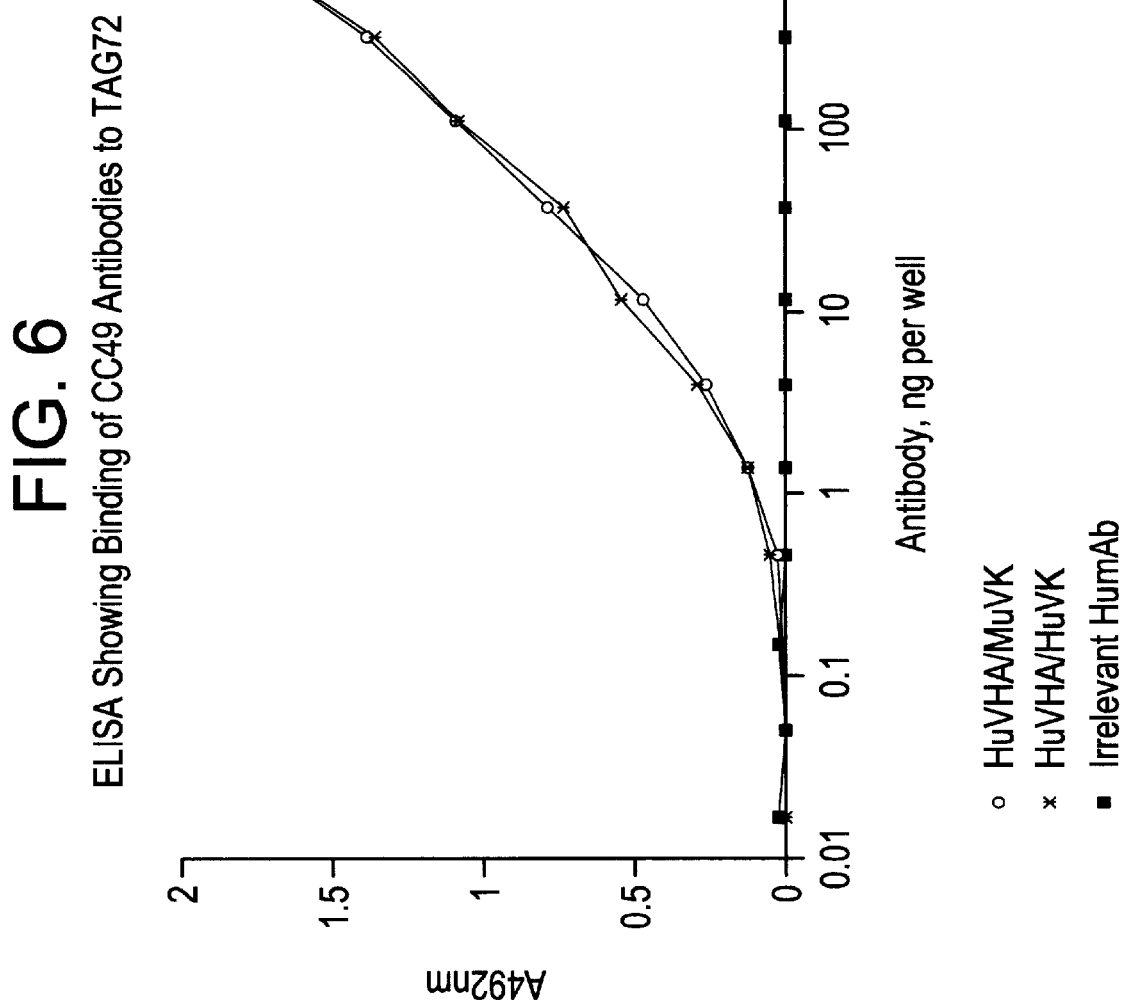
FIG. 6 is an ELISA showing binding of CC49 antibodies HuVHA/MuVK and HuVHA/HuVK to TAG-72.
Figure 7:
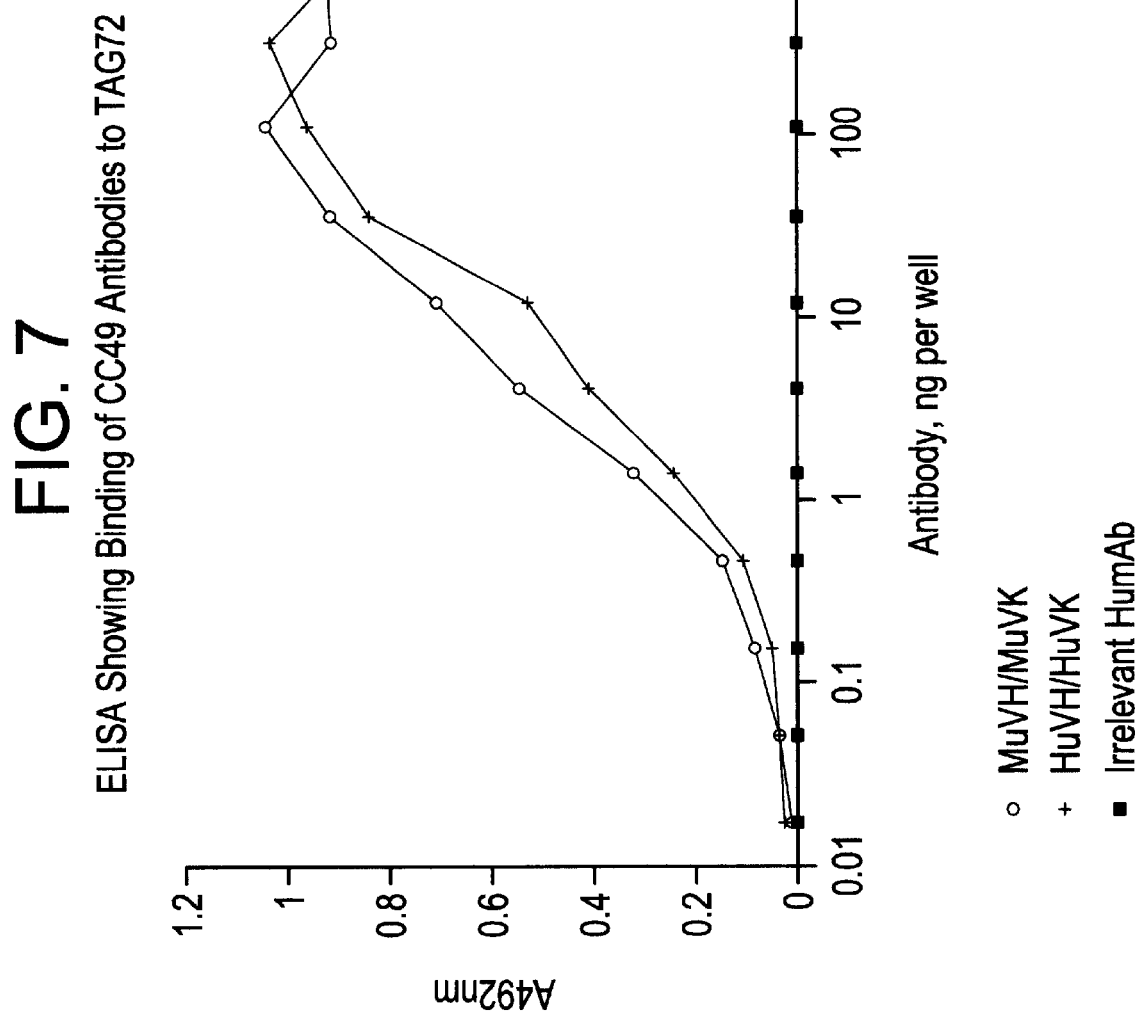
FIG. 7 is an ELISA showing binding of CC49 antibodies MuVH/MuVK and HuVH/HuVK to TAG-72.
Figure 8:
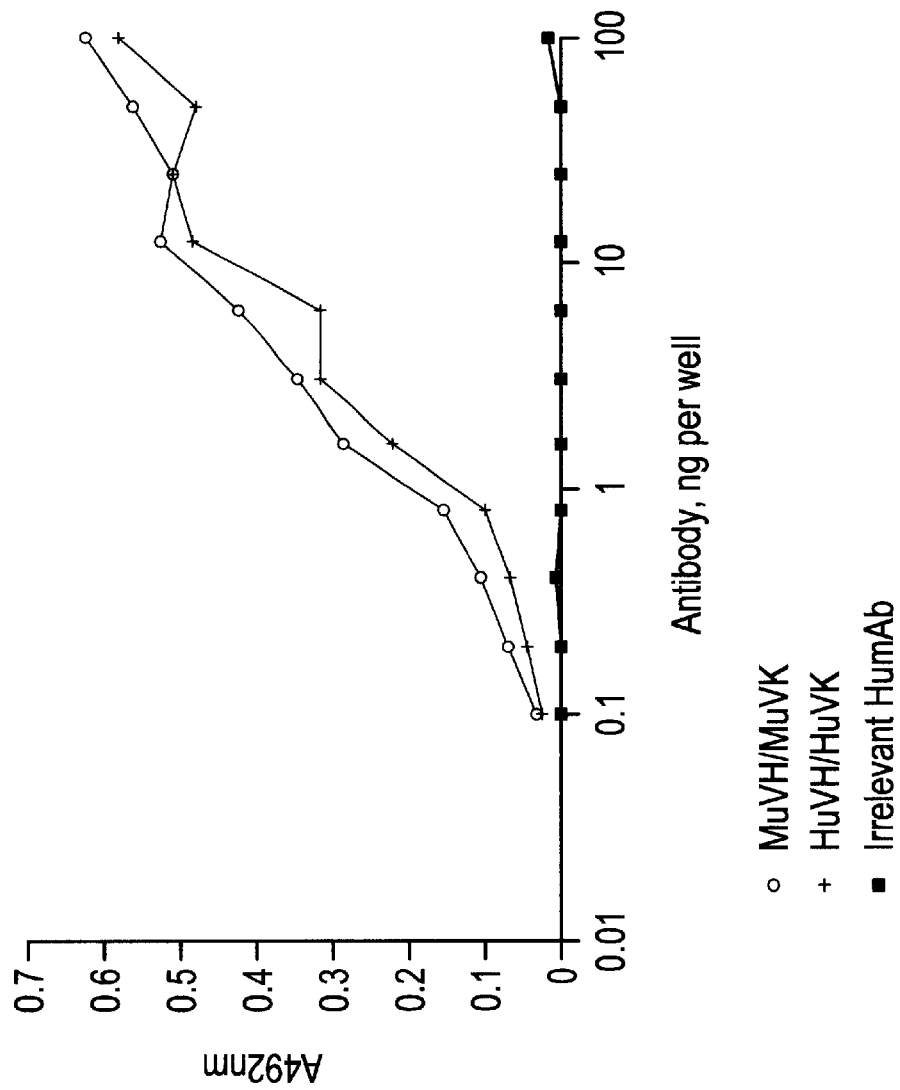
FIG. 8 is an ELISA showing binding of CC49 antibodies MuVH/MuVK and HuVH/HuVK to TAG-72.
Figure 9:
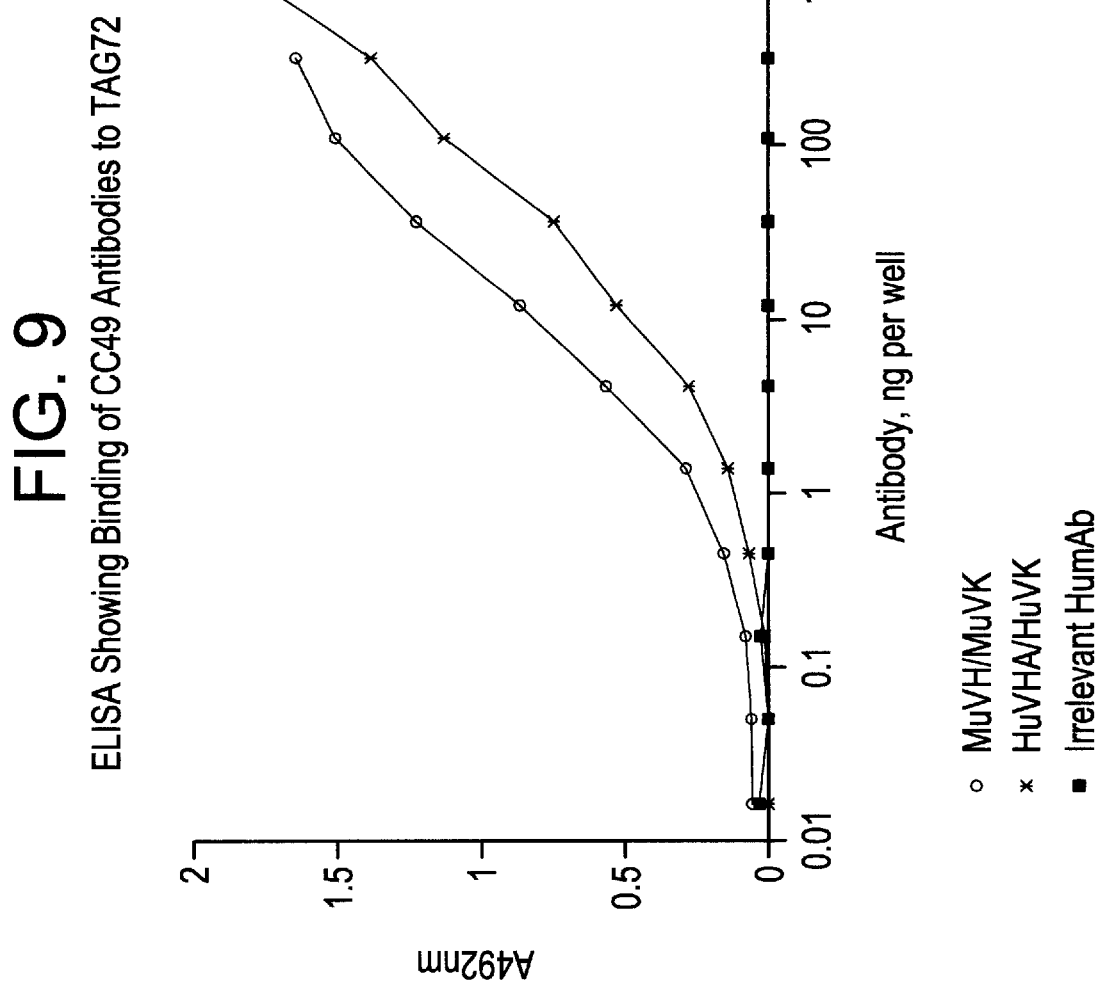
FIG. 9 is an ELISA showing binding of CC49 antibodies MuVH/MuVK and HuVHA/HuVK to TAG-72.

The data in FIG. 6 show that, with HuVHA, the HuVK humanized light chain functions as well as the MuVK chimeric light chain. FIGS. 7 and 8 indicate that the fully humanized HuVH/HuVK antibody binds TAG-72 approximately 2-fold less than the chimeric MuVH/MuVK antibody. Also, FIG. 9 suggests that the A24 mutation produces no enhancement in antigen binding; rather, the A24 mutation causes an approximate 2-fold reduction in affinity as measured by this ELISA assay.

Further Development of Humanized CC49

Because it appears that the HuVK humanized light chain functions as well as the MuVK chimeric light chain, further work was directed to making alternate mutated versions of the HuVH humanized heavy chain. A first variant of HuVH was made by replacing the Lysine residue shown at position 76 of the CC49 NMVH in FIG. 1 with the murine FR residue, serine. This was achieved by the Vent DNA polymerase PCR overlap extension protocol described above, using two primer-and-mutating oligonucleotide pairs— oligonucleotides 10 and 4, and oligonucleotides 11 and 5. Each pair was used in conjunction with one of the strands of a dsDNA template—situated between the HindIII and BamHI sites of plasmid M13—and having the nucleotide sequence shown in FIG. 14 (the upper strand was used with pair 11 & 5). Mutating oligonucleotides 4 and 5 were designed and synthesized with the following sequences:

4. 5'-AGACACCAGCAGCAACCAGTTCAG-3'(SEQ ID NO:30); and 5. 5'-GCTGAACTGGTTGCTGCTGGTGTC-3'(SEQ ID NO:3 1).

The serine residue codons are shown in bold-face type. The resulting humanized CC49 $V_H$ was named "HuVHS."

A second variant of HUVH was made by replacing the threonine residue shown at position 74 of the CC49 NMVH in FIG. 1 with the murine FR residue, Lysine.

This was achieved by the Vent DNA polymerase PCR overlap extension protocol described above, using two primer-and-mutating oligonucleotide pairs— oligonucleotides 10 and 6, and oligonucleotides 11 and 7. Each pair was used in conjunction with one of the strands of a dsDNA template—situated between the HindIII and BamHI sites of plasmid M13—and having the nucleotide sequence shown in FIG. 14 (the upper strand was used with pair 11 & 7). Mutating oligonucleotides 6 and 7 were designed and synthesized with the following sequences.

6. 5'-CTGGCAGACAAGAGCAAGAACCAG-3' (SEQ ID NO:32).

7. 5'-TGGTTCTTGCTCTTGTCTGCCAGC-3'(SEQ ID NO:33).

The Lysine residue codons are shown in bold-face type. The resulting humanized CC49 VH was named "HuVHK."

The two heavy chain constructs, HUVHS and HUVHK, which were situated in M13 vectors, were grown and expressed in TG1 cells. The polypeptide expression products of these constructs were sequenced and the amino acid sequences of these constructs are presented in FIG. 1.

Figure 10:
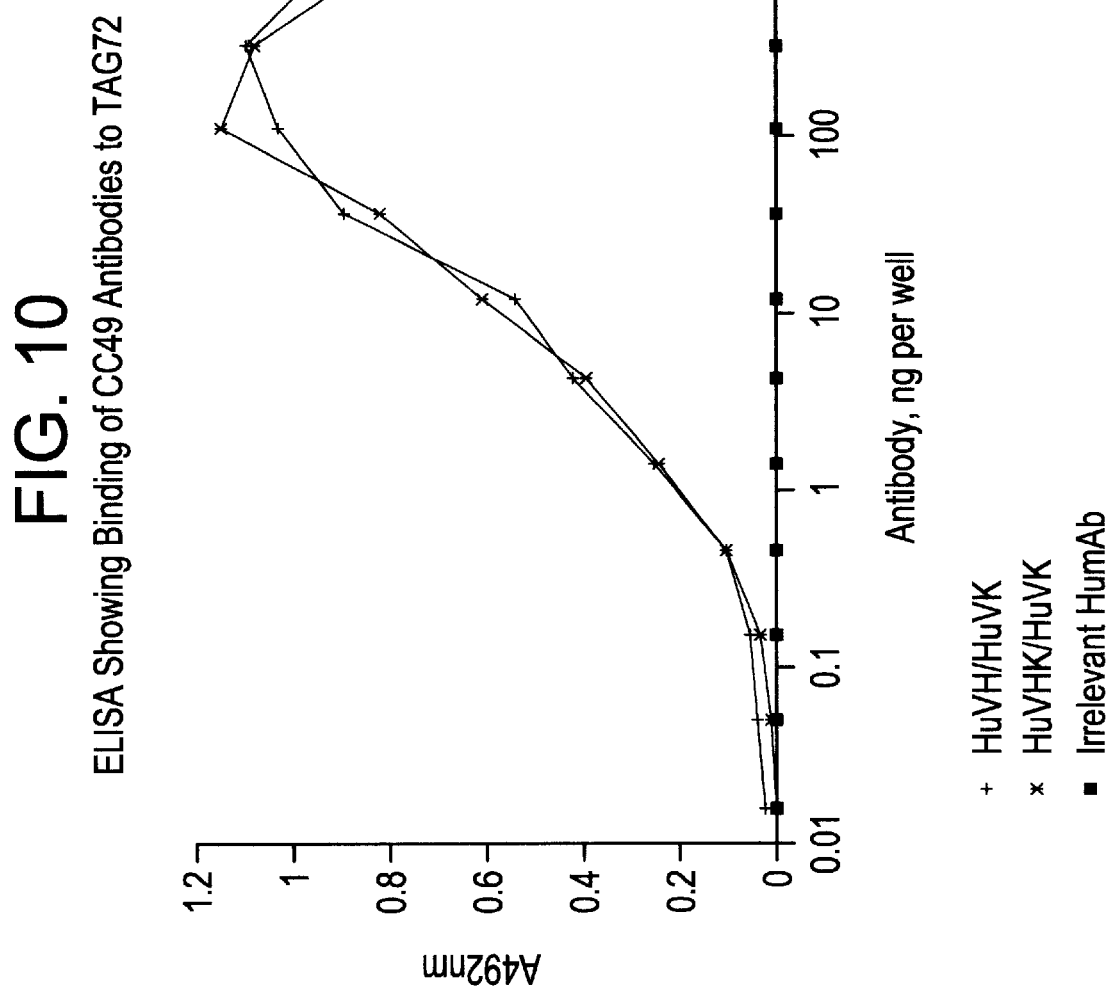
FIG. 10 is an ELISA showing binding of CC49 antibodies HuVH/HuVK and HuVHK/HuVK to TAG-72.
Figure 11:
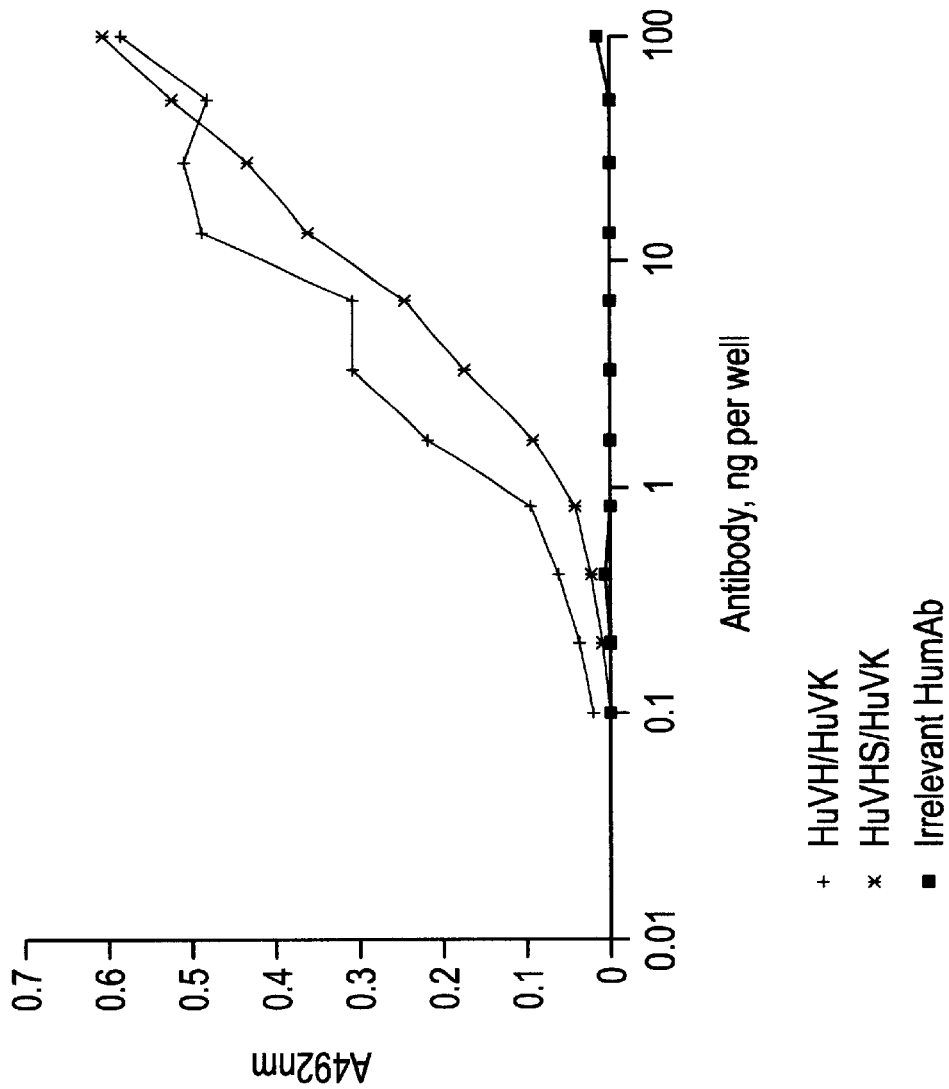

These DNA constructs were then inserted into pSV expression vectors as described above. Combinations of these with HUVK were then inserted into NSO cells. These combinations were expressed and the resulting antibodies were then tested for antigen binding characteristics using the ELISA assay set forth above. The results of these assays are shown in FIGS. 10 and 11. These figures show that neither the K74 nor S76 mutation resulted in enhanced antigen binding; in fact the S76 mutation caused an approximate 2-fold reduction in affinity as measured by this ELISA assay.

Example 2

Measurement of Affinity Constant for the Humanized CC49 Antibody Obtained in Example 1

Figure 12:
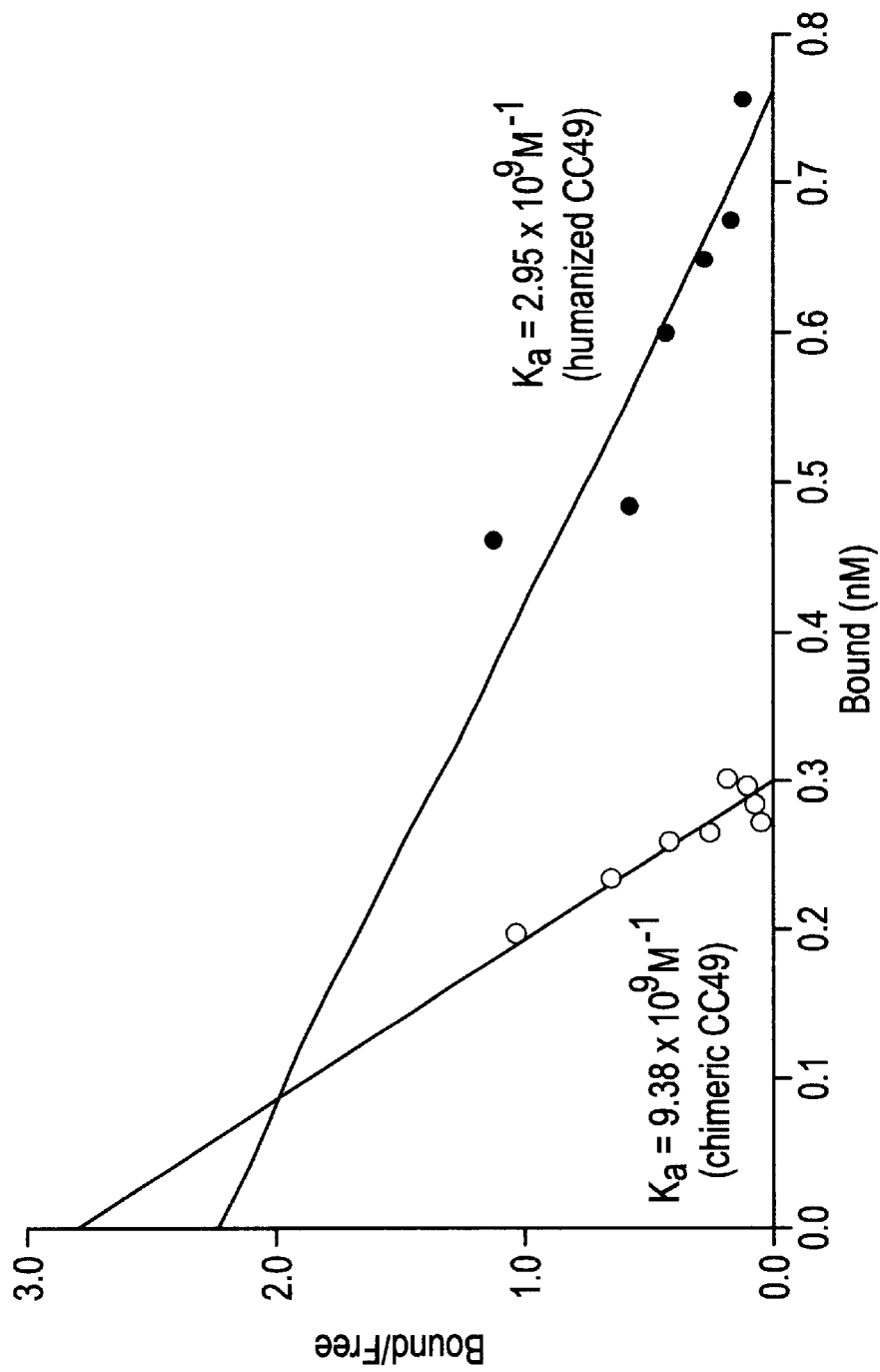
FIG. 12 is a Scatchard analysis of humanized (HuVH/HuVK) and chimeric (MuVH/MuVK) CC49 monoclonal antibodies.

The affinity constant of the final humanized CC49 antibody, CC49 HuVH/HuVK, of Example 1 (having variable heavy and variable light chain sequences shown in FIGS. 3 and 4, respectively) were measured according to the ELISA assay protocol set forth above. The ATCC (Budapest) HB 9884 chimeric CC49 antibody was used as an internal control. This ELISA assay was performed repeatedly using purified samples of humanized and chimeric CC49 monoclonal antibodies in order to substantiate the accuracy of the values obtained and to account for inherent assay-to-assay variability. Typical results from such an analysis are shown in FIG. 12. A summary of the results obtained during these analyses is shown in Table 1.

TABLE 1

Summary of Affinity Constant Analysis of Humanized & Chimeric CC49

|  | Chimeric CC49[1] | CC49 HuVH/HuVK |
|---|---|---|
| Affinity Constant (Ka) | $7.62 \times 10^9 M^{-1}$ | $4.27 \times 10^9 M^{-1}$ |
| ± standard deviation | $3.94 \times 10^9 M^{-1}$ | $2.57 \times 10^9 M^{-1}$ |
| number of analyses | 7 | 8 |

These results demonstrate that the humanized anti-TAG-72 antibody HuVH/HuVK (having the variable heavy and variable light sequences shown in FIGS. 3 and 4, respectively) has a binding affinity approximating that of a chimeric CC49 antibody (MuVH/MuVK). Therefore, it is expected that this humanized antibody will effectively target TAG-72-expressing carcinomas in vivo. Also, based on its sequence this antibody should exhibit little or no immunogenicity in humans, and exhibit advantageous plasma clearance, metabolic properties, and effective tumor targeting in relation to the murine CC49, and also in relation to chimeric versions thereof.

A murine plasmacytoma cell line which produces this humanized CC49 antibody was deposited with the American Type Culture Collection (10801 University Boulevard, Manassas, Va. 20110-2209, on Oct. 16, 1996) and this cell line was accorded accession number ATCC CRL-12209. This deposit was made in accordance with the Budapest Treaty. This deposited cell line will be made irrevocably available, without restriction, upon issuance of a patent to this application or any other application claiming priority to this application under 35 U.S.C. § 120.

Based on the foregoing, it will be appreciated that the humanized antibodies disclosed in Examples 1–3, exhibit antigen-binding characteristics, i.e. TAG-72 affinities comparable to the parent monoclonal antibody, nCC49 (murine antibody), and to chimeric antibodies derived from nCC49, e.g., cCC49. Moreover, based on the foregoing results, these antibodies possess properties which will render them well suited for usage as in vivo diagnostics or therapeutics, e.g., improved serum clearance, metabolic properties, and little or no immunogenicity in humans.

These properties are highly significant because these properties will enable the subject humanized antibodies to be administered repeatedly, in large dosages, and over a prolonged period of time without significant adverse effects, e.g., a HAMA response or non-specific cytotoxicity. This is important for cancer treatment as well as for cancer diagnosis as it enables these antibodies to be used over prolonged time periods. Moreover, the clearance properties of the subject human antibodies will enable these antibodies to effectively target desired target sites, e.g., TAG-72 expressing carcinomas (because of the effects of serum clearance on targeting efficiency). Therefore, the humanized antibodies of the present invention comprise a substantial improvement in relation to previously disclosed antibodies specific to TAG-72.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. An isolated nucleic acid from which may be expressed either:

A) a humanized antibody having binding specificity to TAG-72 wherein said humanized antibody comprises:
      1) at least one NEWM-grafted humanized heavy chain variable region (VH) having the amino acid sequence of any one of SEQ ID NO:3, SEQ ID NO:4, SEQ ID NO:5, and SEQ ID NO:6; and
      2) at least one REI-grafted humadized light chain variable region (VL) having the amino acid sequence of SEQ ID NO:9; or
   B) a hunanized antibody fragment having binding specificity to TAG-72, said fragment being a fragment of the humanized antibody of Part A).

2. An isolated vector comprising a nucleic acid sequence according to claim 1.

3. The vector according to claim 2 wherein said vector is a bare nucleic acid segment, a carrier-associated nucleic acid segment, a nucleoprotein, a plasmid, a virus, a viroid, or a transposable element.

4. The nucleic acid according to claim 1 wherein said humanized antibody is the humanized antibody expressed by a cell deposited as ATCC CRL-12209.

* * * * *

SEQUENCE LISTING

<160> NUMBER OF SEQ ID NOS: 33

<210> SEQ ID NO 1
<211> LENGTH: 115
<212> TYPE: PRT
<213> ORGANISM: Mus musculus
<220> FEATURE:
<221> NAME/KEY: Murine CC49 VH
<222> LOCATION: 1..115

<400> SEQUENCE: 1

Gln Val Gln Leu Gln Gln Ser Asp Ala Glu Leu Val Lys Pro Gly Ala
                 5                  10                  15

Ser Val Lys Ile Ser Cys Lys Ala Ser Gly Tyr Thr Phe Thr Asp His
             20                  25                  30

Ala Ile His Trp Val Lys Gln Asn Pro Glu Gln Gly Leu Glu Trp Ile
         35                  40                  45

Gly Tyr Phe Ser Pro Gly Asn Asp Asp Phe Lys Tyr Asn Glu Arg Phe
     50                  55                  60

Lys Gly Lys Ala Thr Leu Thr Ala Asp Lys Ser Ser Thr Ala Tyr
 65                  70                  75                  80

Val Gln Leu Asn Ser Leu Thr Ser Glu Asp Ser Ala Val Tyr Phe Cys
                 85                  90                  95

Thr Arg Ser Leu Asn Met Ala Tyr Trp Gly Gln Gly Thr Ser Val Thr
            100                 105                 110

Val Ser Ser
        115

<210> SEQ ID NO 2
<211> LENGTH: 115
<212> TYPE: PRT
<213> ORGANISM: Homo sapiens
<220> FEATURE:
<221> NAME/KEY: NEWM VH FR template
<222> LOCATION: 1..115
<223> OTHER INFORMATION: CDR amino acids are indicated by Xaa

<400> SEQUENCE: 2

Gln Val Gln Leu Gln Glu Ser Gly Pro Gly Leu Val Arg Pro Ser Gln
                 5                  10                  15

Thr Leu Ser Leu Thr Cys Thr Val Ser Gly Xaa Xaa Xaa Xaa Xaa
             20                  25                  30

Xaa Xaa Xaa Trp Val Arg Gln Pro Pro Gly Arg Gly Leu Glu Trp Ile
         35                  40                  45

Gly Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Asp Thr Ser Lys Asn Gln Phe Ser
 65                  70                  75                  80

Leu Arg Leu Ser Ser Val Thr Ala Ala Asp Thr Ala Val Tyr Xaa Xaa
                 85                  90                  95

Xaa Xaa Xaa Xaa Xaa Xaa Xaa Trp Gly Gln Gly Ser Leu Val Thr
            100                 105                 110

Val Ser Ser
        115

<210> SEQ ID NO 3
<211> LENGTH: 115
<212> TYPE: PRT

```
<213> ORGANISM: Artificial Sequence
<220> FEATURE:
<221> NAME/KEY: Humanized CC49 VH, HuVH
<222> LOCATION: 1..115
<223> OTHER INFORMATION: Heavy chain variable region containing human
      NEWM FRs and murine CC49 VH CDRs

<400> SEQUENCE: 3

Gln Val Gln Leu Gln Glu Ser Gly Pro Gly Leu Val Arg Pro Ser Gln
                5                  10                  15

Thr Leu Ser Leu Thr Cys Thr Val Ser Gly Tyr Thr Phe Thr Asp His
            20                  25                  30

Ala Ile His Trp Val Arg Gln Pro Pro Gly Arg Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Arg Val Thr Met Leu Ala Asp Thr Ser Lys Asn Gln Phe Ser
65                  70                  75                  80

Leu Arg Leu Ser Ser Val Thr Ala Ala Asp Thr Ala Val Tyr Phe Cys
                85                  90                  95

Thr Arg Ser Leu Asn Met Ala Tyr Trp Gly Gln Gly Ser Leu Val Thr
            100                 105                 110

Val Ser Ser
        115

<210> SEQ ID NO 4
<211> LENGTH: 115
<212> TYPE: PRT
<213> ORGANISM: Artificial Sequence
<220> FEATURE:
<221> NAME/KEY: Humanized CC49 VH, HuVHA
<222> LOCATION: 1..115
<223> OTHER INFORMATION: Heavy chain variable region containing human
      NEWM FRs and murine CC49 VH CDRs, and retaining a murine
      alanine in FR1

<400> SEQUENCE: 4

Gln Val Gln Leu Gln Glu Ser Gly Pro Gly Leu Val Arg Pro Ser Gln
                5                  10                  15

Thr Leu Ser Leu Thr Cys Thr Ala Ser Gly Tyr Thr Phe Thr Asp His
            20                  25                  30

Ala Ile His Trp Val Arg Gln Pro Pro Gly Arg Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Arg Val Thr Met Leu Ala Asp Thr Ser Lys Asn Gln Phe Ser
65                  70                  75                  80

Leu Arg Leu Ser Ser Val Thr Ala Ala Asp Thr Ala Val Tyr Phe Cys
                85                  90                  95

Thr Arg Ser Leu Asn Met Ala Tyr Trp Gly Gln Gly Ser Leu Val Thr
            100                 105                 110

Val Ser Ser
        115

<210> SEQ ID NO 5
<211> LENGTH: 115
<212> TYPE: PRT
<213> ORGANISM: Artificial Sequence
<220> FEATURE:
<221> NAME/KEY: Humanized CC49 VH, HuVHS
<222> LOCATION: 1..115
```

```
<223> OTHER INFORMATION: Heavy chain variable region containing human
      NEWM FRs and murine CC49 VH CDRs, and retaining a murine
      serine in FR3

<400> SEQUENCE: 5

Gln Val Gln Leu Gln Glu Ser Gly Pro Gly Leu Val Arg Pro Ser Gln
                5                   10                  15

Thr Leu Ser Leu Thr Cys Thr Val Ser Gly Tyr Thr Phe Thr Asp His
            20                  25                  30

Ala Ile His Trp Val Arg Gln Pro Pro Gly Arg Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Arg Val Thr Met Leu Ala Asp Thr Ser Ser Asn Gln Phe Ser
 65                  70                  75                  80

Leu Arg Leu Ser Ser Val Thr Ala Ala Asp Thr Ala Val Tyr Phe Cys
                85                  90                  95

Thr Arg Ser Leu Asn Met Ala Tyr Trp Gly Gln Gly Ser Leu Val Thr
            100                 105                 110

Val Ser Ser
        115

<210> SEQ ID NO 6
<211> LENGTH: 115
<212> TYPE: PRT
<213> ORGANISM: Artificial Sequence
<220> FEATURE:
<221> NAME/KEY: Humanized CC49 VH, HuVHK
<222> LOCATION: 1..115
<223> OTHER INFORMATION: Heavy chain variable region containing human
      NEWM FRs and murine CC49 VH CDRs, and retaining a murine
      lysine in FR3

<400> SEQUENCE: 6

Gln Val Gln Leu Gln Glu Ser Gly Pro Gly Leu Val Arg Pro Ser Gln
                5                   10                  15

Thr Leu Ser Leu Thr Cys Thr Val Ser Gly Tyr Thr Phe Thr Asp His
            20                  25                  30

Ala Ile His Trp Val Arg Gln Pro Pro Gly Arg Gly Leu Glu Trp Ile
        35                  40                  45

Gly Tyr Phe Ser Pro Gly Asn Asp Asp Phe Lys Tyr Asn Glu Arg Phe
    50                  55                  60

Lys Gly Arg Val Thr Met Leu Ala Asp Lys Ser Lys Asn Gln Phe Ser
 65                  70                  75                  80

Leu Arg Leu Ser Ser Val Thr Ala Ala Asp Thr Ala Val Tyr Phe Cys
                85                  90                  95

Thr Arg Ser Leu Asn Met Ala Tyr Trp Gly Gln Gly Ser Leu Val Thr
            100                 105                 110

Val Ser Ser
        115

<210> SEQ ID NO 7
<211> LENGTH: 113
<212> TYPE: PRT
<213> ORGANISM: Mus musculus
<220> FEATURE:
<221> NAME/KEY: Murine CC49 VK
<222> LOCATION: 1..113

<400> SEQUENCE: 7
```

-continued

```
Asp Ile Val Met Ser Gln Ser Pro Ser Ser Leu Pro Val Ser Val Gly
                 5                   10                  15

Glu Lys Val Thr Leu Ser Cys Lys Ser Ser Gln Ser Leu Leu Tyr Ser
                20                  25                  30

Gly Asn Gln Lys Asn Tyr Leu Ala Trp Tyr Gln Gln Lys Pro Gly Gln
            35                  40                  45

Ser Pro Lys Leu Leu Ile Tyr Trp Ala Ser Ala Arg Glu Ser Gly Val
        50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
                100                 105                 110

Lys
```

<210> SEQ ID NO 8
<211> LENGTH: 113
<212> TYPE: PRT
<213> ORGANISM: Homo sapiens
<220> FEATURE:
<221> NAME/KEY: REI VK FR template
<222> LOCATION: 1..113
<223> OTHER INFORMATION: CDR amino acids are indicated by Xaa

<400> SEQUENCE: 8

```
Asp Ile Gln Leu Thr Gln Ser Pro Ser Leu Ser Ala Ser Val Gly
                 5                   10                  15

Asp Arg Val Thr Ile Thr Cys Lys Ser Ser Xaa Xaa Xaa Xaa Xaa Xaa
                20                  25                  30

Xaa Xaa Xaa Lys Asn Tyr Leu Ala Trp Tyr Gln Gln Thr Pro Gly Lys
            35                  40                  45

Ala Pro Lys Leu Leu Ile Tyr Trp Ala Xaa Xaa Xaa Glu Ser Gly Val
        50                  55                  60

Pro Ser Arg Phe Ser Gly Ser Gly Ser Gly Thr Asp Tyr Thr Phe THr
65                  70                  75                  80

Ile Ser Ser Leu Gln Pro Glu Asp Ile Ala Thr Tyr Tyr Cys Xaa Xaa
                85                  90                  95

Xaa Xaa Xaa Xaa Xaa Xaa Xaa Phe Gly Gln Gly Thr Lys Leu Gln Ile
                100                 105                 110

Thr
```

<210> SEQ ID NO 9
<211> LENGTH: 113
<212> TYPE: PRT
<213> ORGANISM: Artificial Sequence
<220> FEATURE:
<221> NAME/KEY: Humanized CC49 VK, HuVK
<222> LOCATION: 1..113
<223> OTHER INFORMATION: Light chain variable region containing human
      REI FRs and murine CC49 VL CDRs

<400> SEQUENCE: 9

```
Asp Ile Gln Met Thr Gln Ser Pro Ser Ser Leu Ser Ala Ser Val Gly
                 5                   10                  15

Asp Arg Val Thr Ile Thr Cys Lys Ser Ser Gln Ser Leu Leu Tyr Ser
                20                  25                  30

Gly Asn Gln Lys Asn Tyr Leu Ala Trp Tyr Gln Gln Thr Pro Gly Lys
            35                  40                  45
```

```
Ala Pro Lys Leu Leu Ile Tyr Trp Ala Ser Ala Arg Glu Ser Gly Val
            50                  55                  60

Pro Ser Arg Phe Ser Gly Ser Gly Ser Gly Thr Asp Tyr Thr Phe Thr
 65                  70                  75                  80

Ile Ser Ser Leu Gln Pro Glu Asp Ile Ala Thr Tyr Tyr Cys Gln Gln
                 85                  90                  95

Tyr Tyr Ser Tyr Pro Leu Thr Phe Gly Gln Gly Thr Lys Leu Gln Ile
            100                 105                 110

Thr

<210> SEQ ID NO 10
<211> LENGTH: 115
<212> TYPE: PRT
<213> ORGANISM: Mus musculus
<220> FEATURE:
<221> NAME/KEY: Murine CC49 VH
<222> LOCATION: 1..115

<400> SEQUENCE: 10

Gln Val Gln Leu Gln Gln Ser Asp Ala Glu Leu Val Lys Pro Gly Ala
                 5                  10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Phe
 50                  55                  60

Lys Gly Lys Ala Thr Leu Thr Ala Asp Lys Ser Ser Ser Thr Ala Tyr
 65                  70                  75                  80

Val Gln Leu Asn Ser Leu Thr Ser Glu Asp Ser Ala Val Tyr Phe Cys
                 85                  90                  95

Thr Arg Ser Leu Asn Met Ala Tyr Trp Gly Gln Gly Thr Ser Val Thr
            100                 105                 110

Val Ser Ser
        115

<210> SEQ ID NO 11
<211> LENGTH: 115
<212> TYPE: PRT
<213> ORGANISM: Artificial Sequence
<220> FEATURE:
<221> NAME/KEY: HuCC49 VH
<222> LOCATION: 1..115
<223> OTHER INFORMATION: Heavy chain variable region containing human
      NEWM FRs and murine CC49 VH CDRs

<400> SEQUENCE: 11

Gln Val Gln Leu Gln Glu Ser Gly Pro Gly Leu Val Arg Pro Ser Gln
                 5                  10                  15

Thr Leu Ser Leu Thr Cys Thr Val Ser Gly Tyr Thr Phe Thr Asp His
            20                  25                  30

Ala Ile His Trp Val Arg Gln Pro Pro Gly Arg Gly Leu Glu Trp Ile
        35                  40                  45

Gly Tyr Phe Ser Pro Gly Asn Asp Asp Phe Lys Tyr Asn Glu Arg Phe
 50                  55                  60

Lys Gly Arg Val Thr Met Leu Ala Asp Thr Ser Lys Asn Gln Phe Ser
 65                  70                  75                  80

Leu Arg Leu Ser Ser Val Thr Ala Ala Asp Thr Ala Val Tyr Phe Cys
```

```
                    85                  90                  95
Thr Arg Ser Leu Asn Met Ala Tyr Trp Gly Gln Gly Ser Leu Val Thr
               100                 105                 110

Val Ser Ser
       115

<210> SEQ ID NO 12
<211> LENGTH: 117
<212> TYPE: PRT
<213> ORGANISM: Homo sapiens
<220> FEATURE:
<221> NAME/KEY: NEWM VH
<222> LOCATION: 1..117

<400> SEQUENCE: 12

Gln Val Gln Leu Glu Gln Ser Gly Pro Gly Leu Val Arg Pro Ser Gln
1               5                  10                   15

Thr Leu Ser Leu Thr Cys Thr Val Ser Gly Ser Thr Phe Ser Asn Asp
              20                  25                  30

Tyr Tyr Thr Trp Val Arg Gln Pro Pro Gly Arg Gly Leu Glu Trp Ile
           35                  40                  45

Gly Tyr Val Phe Tyr His Gly Thr Ser Asp Thr Thr Pro Leu Arg
     50                  55                  60

Ser Arg Val Thr Met Leu Val Asp Thr Ser Lys Asn Gln Phe Ser Leu
65                   70                  75                   80

Arg Leu Ser Ser Val Thr Ala Ala Asp Thr Ala Val Tyr Tyr Cys Ala
                 85                  90                  95

Arg Asn Leu Ile Ala Gly Cys Ile Asp Val Trp Gly Gln Gly Ser Leu
               100                 105                 110

Val Thr Val Ser Ser
           115

<210> SEQ ID NO 13
<211> LENGTH: 113
<212> TYPE: PRT
<213> ORGANISM: Mus musculus
<220> FEATURE:
<221> NAME/KEY: Murine CC49 VL
<222> LOCATION: 1..113

<400> SEQUENCE: 13

Asp Ile Val Met Ser Gln Ser Pro Ser Ser Leu Pro Val Ser Val Gly
1               5                  10                   15

Glu Lys Val Thr Leu Ser Cys Lys Ser Ser Gln Ser Leu Leu Tyr Ser
              20                  25                  30

Gly Asn Gln Lys Asn Tyr Leu Ala Trp Tyr Gln Gln Lys Pro Gly Gln
           35                  40                  45

Ser Pro Lys Leu Leu Ile Tyr Trp Ala Ser Ala Arg Glu Ser Gly Val
     50                  55                  60

Pro Asp Arg Phe Thr Gly Ser Gly Ser Gly Thr Asp Phe Thr Leu Ser
65                   70                  75                   80

Ile Ser Ser Val Lys Thr Glu Asp Leu Ala Val Tyr Tyr Cys Gln Gln
                 85                  90                  95

Tyr Tyr Ser Tyr Pro Leu Thr Phe Gly Ala Gly Thr Lys Leu Val Leu
               100                 105                 110

Lys

<210> SEQ ID NO 14
```

-continued

```
<211> LENGTH: 113
<212> TYPE: PRT
<213> ORGANISM: Artificial Sequence
<220> FEATURE:
<221> NAME/KEY: HuCC49 VL
<222> LOCATION: 1..113
<223> OTHER INFORMATION: Light chain variable region containing human
      REI FRs and murine CC49 VL CDRs

<400> SEQUENCE: 14

Asp Ile Gln Met Thr Gln Ser Pro Ser Ser Leu Ser Ala Ser Val Gly
                 5                  10                  15

Asp Arg Val Thr Ile Thr Cys Lys Ser Gln Ser Leu Leu Tyr Ser
             20                  25                  30

Gly Asn Gln Lys Asn Tyr Leu Ala Trp Tyr Gln Gln Thr Pro Gly Lys
         35                  40                  45

Ala Pro Lys Leu Leu Ile Tyr Trp Ala Ser Ala Arg Glu Ser Gly Val
     50                  55                  60

Pro Ser Arg Phe Ser Gly Ser Gly Ser Gly Thr Asp Tyr Thr Phe Thr
 65                  70                  75                  80

Ile Ser Ser Leu Gln Pro Glu Asp Ile Ala Thr Tyr Tyr Cys Gln Gln
                 85                  90                  95

Tyr Tyr Ser Tyr Pro Leu Thr Phe Gly Gln Gly Thr Lys Leu Gln Ile
            100                 105                 110

Thr

<210> SEQ ID NO 15
<211> LENGTH: 107
<212> TYPE: PRT
<213> ORGANISM: Homo sapiens
<220> FEATURE:
<221> NAME/KEY: REI VL
<222> LOCATION: 1..107

<400> SEQUENCE: 15

Asp Ile Gln Met Thr Gln Ser Pro Ser Ser Leu Ser Ala Ser Val Gly
                 5                  10                  15

Asp Arg Val Thr Ile Thr Cys Gln Ala Ser Gln Asp Ile Ile Lys Tyr
             20                  25                  30

Leu Asn Trp Tyr Gln Gln Thr Pro Gly Lys Ala Pro Lys Leu Leu Ile
         35                  40                  45

Tyr Glu Ala Ser Asn Leu Gln Ala Gly Val Pro Ser Arg Phe Ser Gly
     50                  55                  60

Ser Gly Ser Gly Thr Asp Tyr Thr Phe Thr Ile Ser Ser Leu Gln Pro
 65                  70                  75                  80

Glu Asp Ile Ala Thr Tyr Tyr Cys Gln Gln Tyr Gln Ser Leu Pro Tyr
                 85                  90                  95

Thr Phe Gly Gln Gly Thr Lys Leu Gln Ile Thr
            100                 105

<210> SEQ ID NO 16
<211> LENGTH: 345
<212> TYPE: DNA
<213> ORGANISM: Homo sapiens
<220> FEATURE:
<221> NAME/KEY: Template used to produce HuVH and HuVHA
<222> LOCATION: 1..345
<223> OTHER INFORMATION: CDR amino acid-encoding codons are indicated
      by NNN

<400> SEQUENCE: 16 cag gtc caa ctg cag gag agc ggt cca ggt ctt gtg aga cct agc cag       48
```

```
acc ctg agc ctg acc tgc acc gtg tct ggc nnn nnn nnn nnn nnn nnn      96 nnn nnn nnn tgg gtg aga cag cca cct gga cga ggt ctt gag tgg att     144 gga nnn nnn nnn nnn nnn nnn nnn nnn nnn nnn nnn nnn nnn nnn         192 nnn nnn nnn nnn nnn nnn nnn nnn gac acc agc aag aac cag ttc agc     240 ctg aga ctc agc agc gtg aca gcc gcc gac acc gcg gtc tat nnn nnn     288 nnn nnn nnn nnn nnn nnn nnn nnn tgg ggc caa ggg tcc ttg gtc acc     336 gtc tcc tca                                                         345

<210> SEQ ID NO 17
<211> LENGTH: 345
<212> TYPE: DNA
<213> ORGANISM: Artificial Sequence
<220> FEATURE:
<221> NAME/KEY: Template used to produce HuVHS and HuVHK
<222> LOCATION: 1..345
<223> OTHER INFORMATION: DNA encoding a humanized heavy chain variable
      region containing human NEWM FRs and murine CC49 VH CDRs

<400> SEQUENCE: 17 cag gtc caa ctg cag gag agc ggt cca ggt ctt gtg aga cct agc cag      48 acc ctg agc ctg acc tgc acc gtg tct ggc tac acc ttc act gac cat      96 gca att cac tgg gtg aga cag cca cct gga cga ggt ctt gag tgg att     144 gga tat ttt tct ccc gga aat gat gat ttt aaa tac aat gag agg ttc     192 aag ggg aga gtg aca atg ctg gca gac acc agc aag aac cag ttc agc     240 ctg aga ctc agc agc gtg aca gcc gcc gac acc gcg gtc tat ttc tgt     288 aca aga tcc ctg aat atg gcc tac tgg ggc caa ggg tcc ttg gtc acc     336 gtc tcc tca                                                         345

<210> SEQ ID NO 18
<211> LENGTH: 17
<212> TYPE: DNA
<213> ORGANISM: Artificial Sequence
<220> FEATURE:
<221> NAME/KEY: Oligonucleotide 10
<222> LOCATION: 1..17
<223> OTHER INFORMATION: Oligonucleotide primer for plasmid M13

<400> SEQUENCE: 18
ctaaaacgac ggccagt                                                   17

<210> SEQ ID NO 19
<211> LENGTH: 16
<212> TYPE: DNA
<213> ORGANISM: Artificial Sequence
<220> FEATURE:
<221> NAME/KEY: Oligonucleotide 11
<222> LOCATION: 1..16
<223> OTHER INFORMATION: Oligonucleotide primer for plasmid M13

<400> SEQUENCE: 19
aacagctatg accatg                                                    16

<210> SEQ ID NO 20
<211> LENGTH: 22
<212> TYPE: DNA
<213> ORGANISM: Artificial Sequence
<220> FEATURE:
<221> NAME/KEY: Oligonucleotide 385
```

```
<222> LOCATION: 1..22
<223> OTHER INFORMATION: Oligonucleotide primer for plasmid M13

<400> SEQUENCE: 20
gcgggcctct tcgctattac gc                                         22

<210> SEQ ID NO 21
<211> LENGTH: 22
<212> TYPE: DNA
<213> ORGANISM: Artificial Sequence
<220> FEATURE:
<221> NAME/KEY: Oligonucleotide 391
<222> LOCATION: 1..22
<223> OTHER INFORMATION: Oligonucleotide primer for plasmid M13

<400> SEQUENCE: 21
ctctctcagg gccaggcggt ga                                         22

<210> SEQ ID NO 22
<211> LENGTH: 60
<212> TYPE: DNA
<213> ORGANISM: Artificial Sequence
<220> FEATURE:
<221> NAME/KEY: Oligonucleotide 1a
<222> LOCATION: 1..60
<223> OTHER INFORMATION: Mutagenic oligonucleotide for retaining 2
      murine FR amino acids in a humanized VH

<400> SEQUENCE: 22
gctgtctcac ccagtgaatt gcatggtcag tgaaggtgta gccagacacg gtgcaggtca  60

<210> SEQ ID NO 23
<211> LENGTH: 60
<212> TYPE: DNA
<213> ORGANISM: Artificial Sequence
<220> FEATURE:
<221> NAME/KEY: Oligonucleotide 1b
<222> LOCATION: 1..60
<223> OTHER INFORMATION: Mutagenic oligonucleotide for retaining 3
      murine FR amino acids in a humanized VH

<400> SEQUENCE: 23
gctgtctcac ccagtgaatt gcatggtcag tgaaggtgta gccagagcgg gtgcaggtca  60

<210> SEQ ID NO 24
<211> LENGTH: 94
<212> TYPE: DNA
<213> ORGANISM: Artificial Sequence
<220> FEATURE:
<221> NAME/KEY: Oligonucleotide 2
<222> LOCATION: 1..94
<223> OTHER INFORMATION: Mutagenic oligonucleotide for retaining 1
      murine FR amino acid in a humanized VH

<400> SEQUENCE: 24
ctggtgtctg ccagcattgt cactctcccc ttgaacctct cattgtattt aaaatcatca  60
tttccgggag aaaaatatcc aatccactca agac                             94

<210> SEQ ID NO 25
<211> LENGTH: 60
<212> TYPE: DNA
<213> ORGANISM: Artificial Sequence
<220> FEATURE:
<221> NAME/KEY: Oligonucleotide 3
<222> LOCATION: 1..60
<223> OTHER INFORMATION: Mutagenic oligonucleotide for retaining 2
      murine FR amino acids in a humanized VH
```

-continued

```
<400> SEQUENCE: 25
ggacccttgg ccccagtagg ccatattcag ggatcttgta cagaaataga ccgcggtgtc        60

<210> SEQ ID NO 26
<211> LENGTH: 39
<212> TYPE: DNA
<213> ORGANISM: Artificial Sequence
<220> FEATURE:
<221> NAME/KEY: Oligonucleotide 21
<222> LOCATION: 1..39
<223> OTHER INFORMATION: Mutagenic oligonucleotide for retaining
      murine CDR amino acids in a humanized VL

<400> SEQUENCE: 26
gttcttctga ttaccactgt ataaaagact tgactggac                               39

<210> SEQ ID NO 27
<211> LENGTH: 26
<212> TYPE: DNA
<213> ORGANISM: Artificial Sequence
<220> FEATURE:
<221> NAME/KEY: Oligonucleotide 22
<222> LOCATION: 1..26
<223> OTHER INFORMATION: Mutagenic oligonucleotide for retaining
      murine CDR amino acids in a humanized VL

<400> SEQUENCE: 27
cagattccct agcggatgcc cagtag                                             26

<210> SEQ ID NO 28
<211> LENGTH: 78
<212> TYPE: DNA
<213> ORGANISM: Artificial Sequence
<220> FEATURE:
<221> NAME/KEY: Oligonucleotide 23
<222> LOCATION: 1..78
<223> OTHER INFORMATION: Mutagenic oligonucleotide for retaining
      murine CDR amino acids in a humanized VL

<400> SEQUENCE: 28
ttctactcac gtgtgatttg cagcttggtc ccttggccga acgtgagggg ataggaatag        60
tattgctggc agtagtag                                                      78

<210> SEQ ID NO 29
<211> LENGTH: 23
<212> TYPE: DNA
<213> ORGANISM: Artificial Sequence
<220> FEATURE: Oligonucleotide 24used to produce HuVHS and HuVHK
<222> LOCATION: 1..23
<223> OTHER INFORMATION: Mutagenic oligonucleotide for retaining murine
      CDR amino acids in a humanized VL

<400> SEQUENCE: 29
gctctgggtc atctggatgt cgg                                                23

<210> SEQ ID NO 30
<211> LENGTH: 24
<212> TYPE: DNA
<213> ORGANISM: Artificial Sequence
<220> FEATURE:
<221> NAME/KEY: Oligonucleotide 4
<222> LOCATION: 1..24
<223> OTHER INFORMATION: Mutagenic oligonucleotide for retaining a
      murine serine in FR3 of HuVHS

<400> SEQUENCE: 30
agacaccagc agcaaccagt tcag                                               24
```

```
<210> SEQ ID NO 31
<211> LENGTH: 24
<212> TYPE: DNA
<213> ORGANISM: Artificial Sequence
<220> FEATURE:
<221> NAME/KEY: Oligonucleotide 5
<222> LOCATION: 1..24
<223> OTHER INFORMATION: Mutagenic oligonucleotide for retaining a
      murine serine in FR3 of HuVHS

<400> SEQUENCE: 31
gctgaactgg ttgctgctgg tgtc                                          24

<210> SEQ ID NO 32
<211> LENGTH: 24
<212> TYPE: DNA
<213> ORGANISM: Artificial Sequence
<220> FEATURE:
<221> NAME/KEY: Oligonucleotide 6
<222> LOCATION: 1..24
<223> OTHER INFORMATION: Mutagenic oligonucleotide for retaining a
      murine lysine in FR3 of HuVHK

<400> SEQUENCE: 32
ctggcagaca agagcaagaa ccag                                          24

<210> SEQ ID NO 33
<211> LENGTH: 24
<212> TYPE: DNA
<213> ORGANISM: Artificial Sequence
<220> FEATURE:
<221> NAME/KEY: Oligonucleotide 7
<222> LOCATION: 1..24
<223> OTHER INFORMATION: Mutagenic oligonucleotide for retaining a
      murine lysine in FR3 of HuVHK

<400> SEQUENCE: 33
tggttcttgc tcttgtctgc cagc                                          24
```